US006613580B1

(12) United States Patent
Chow et al.

(10) Patent No.: US 6,613,580 B1
(45) Date of Patent: Sep. 2, 2003

(54) MICROFLUIDIC SYSTEMS AND METHODS FOR DETERMINING MODULATOR KINETICS

(75) Inventors: Andrea W. Chow, Los Altos, CA (US); Anne R. Kopf-Sill, Portola Valley, CA (US); J. Wallace Parce, Palo Alto, CA (US)

(73) Assignee: Caliper Technologies Corp., Mountain View, CA (US)

( * ) Notice: Subject to any disclaimer, the term of this patent is extended or adjusted under 35 U.S.C. 154(b) by 300 days.

(21) Appl. No.: 09/609,030

(22) Filed: Jun. 30, 2000

Related U.S. Application Data

(60) Provisional application No. 60/142,984, filed on Jul. 6, 1999.

(51) Int. Cl.[7] .................................................. C01N 1/10
(52) U.S. Cl. .................. 436/180; 436/167; 436/172; 436/174; 436/179; 422/68.1; 422/82.05; 422/99
(58) Field of Search ............... 422/55, 68.1, 82.05, 422/83, 100, 99, 102; 436/164, 172, 174, 179, 180

(56) References Cited

U.S. PATENT DOCUMENTS

| 4,390,403 A | 6/1983 | Batchelder |
| 4,908,112 A | 3/1990 | Pace |
| 5,126,022 A | 6/1992 | Soane et al. |
| 5,498,392 A | 3/1996 | Wilding et al. |
| 5,547,849 A | 8/1996 | Baer et al. |
| 5,571,410 A | 11/1996 | Swedberg et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,603,351 A | 2/1997 | Cherukuri et al. |
| 5,635,358 A | 6/1997 | Wilding et al. |

(List continued on next page.)

FOREIGN PATENT DOCUMENTS

| WO | WO 98/00705 | 1/1998 |
| WO | WO 98/00707 | 1/1998 |

(List continued on next page.)

OTHER PUBLICATIONS

Kopp, et al., (1998) "Chemical Amplification: Continuous–Flow PCR on a Chip," *Science* 280:1046.

Koshland, et al. (1966) "Comparison of Experimental Binding Data and Theoretical Models in Proteins Containing Subunits," *Biochemistry* 5:365–385.

Monod, et al.(1965) "On the Nature of Allosteric Transitions: A Plausible Model," *J. Mol. Biol.* 12:88–118.

Cohen, C.B. et al., "A Microchip–Based Enzyme Assay for Protein Kinase A," *Anal. Chem.* (1999) 273:89–97.

Dasgupta, P.K. et al., "Electroosmosis: A Reliable Fluid Propulsion System for Flow Injection Analysis," *Anal. Chem.* (1994) 66:1792–1798.

Jacobson, S.C. et al., "Fused Quartz Substrates for Microchip Electrophoresis," *Anal. Chem.* (1995) 67:2059–2063.

Manz, A. et al., "Electroosmotic pumping and electrophoretic separations for miniaturized chemical analysis systems," *J. Micromech. Microeng.* (1994) 4:257–265.

(List continued on next page.)

*Primary Examiner*—Jill Warden
*Assistant Examiner*—Dwayne K Handy
(74) *Attorney, Agent, or Firm*—Quine Intellectual Property Law Group, P.C.; Matthew B. Murphy; Andrew L. Filler

(57) ABSTRACT

Methods, systems, kits, and apparatus for calculating kinetic and concentration information in microscale systems are provided. Dwell times for access by a microfluidic system are varied and the resulting modulation of signal profile information used to provide a first order estimation of an activity of a potential activity modulator accessed by the system.

30 Claims, 4 Drawing Sheets

U.S. PATENT DOCUMENTS

| | | |
|---|---|---|
| 5,637,469 A | 6/1997 | Wilding et al. |
| 5,699,157 A | 12/1997 | Parce |
| 5,731,212 A | 3/1998 | Gavin et al. |
| 5,750,015 A | 5/1998 | Soane et al. |
| 5,779,868 A | 7/1998 | Parce et al. |
| 5,783,740 A | 7/1998 | Tawarayama et al. |
| 5,800,690 A | 9/1998 | Chow et al. |
| 5,842,787 A | 12/1998 | Kopf-Sill et al. |
| 5,852,495 A | 12/1998 | Parce |
| 5,866,804 A | 2/1999 | O'Keefe |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 5,885,470 A | 3/1999 | Parce et al. |
| 5,942,443 A | 8/1999 | Parce et al. |
| 5,948,227 A | 9/1999 | Dubrow |
| 5,948,684 A * | 9/1999 | Weigl et al. ............ 436/52 |
| 5,955,028 A | 9/1999 | Chow |
| 5,957,579 A | 9/1999 | Kopf-Sill et al. |
| 5,958,203 A | 9/1999 | Parce et al. |
| 5,958,694 A | 9/1999 | Nikiforov |
| 5,959,291 A | 9/1999 | Jensen |
| 5,964,995 A | 10/1999 | Nikiforov et al. |
| 5,965,001 A | 10/1999 | Chow et al. |
| 5,965,410 A | 10/1999 | Chow et al. |
| 5,972,187 A | 10/1999 | Parce et al. |
| 5,972,710 A * | 10/1999 | Weigl et al. ............ 436/34 |
| 5,974,867 A * | 11/1999 | Forster et al. ............ 73/61.41 |
| 5,976,336 A | 11/1999 | Dubrow et al. |
| 5,989,402 A | 11/1999 | Chow et al. |
| 6,001,231 A | 12/1999 | Kopf-Sill |
| 6,004,515 A | 12/1999 | Parce et al. |
| 6,007,690 A * | 12/1999 | Nelson et al. ............ 204/601 |
| 6,011,252 A | 1/2000 | Jensen |
| 6,012,902 A | 1/2000 | Parce |
| 6,037,130 A | 3/2000 | Tyagi et al. |
| 6,042,710 A | 3/2000 | Dubrow |
| 6,046,056 A | 4/2000 | Parce et al. |
| 6,068,752 A | 5/2000 | Dubrow et al. |
| 6,071,478 A | 6/2000 | Chow |
| 6,074,725 A | 6/2000 | Kennedy |
| 6,080,295 A | 6/2000 | Parce et al. |
| 6,103,199 A * | 8/2000 | Bjornson et al. ............ 422/100 |
| 6,136,272 A * | 10/2000 | Weigl et al. ............ 422/82.05 |
| 6,159,739 A * | 12/2000 | Weigl et al. ............ 436/52 |
| 6,284,113 B1 * | 9/2001 | Bjornson et al. ............ 204/453 |
| 6,303,343 B1 | 10/2001 | Kopf-Sill |

FOREIGN PATENT DOCUMENTS

| | | |
|---|---|---|
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |
| WO | WO 99/56954 | 11/1999 |
| WO | WO 99/64848 | 12/1999 |
| WO | WO 00/09753 | 2/2000 |
| WO | WO 00/73799 | 12/2000 |
| WO | WO 01/14064 | 3/2001 |
| WO | WO 01/88195 | 11/2001 |

OTHER PUBLICATIONS

Ramsey, J.M. et al., "Microfabricated chemical measurement systems," *Nature Med.* (1995) 1:1093–1096.

Seiler, K. et al., "Planar Glass Chips for Capillary Electrophoresis: Repetitive Sample Injection, Quantitation, and Separation Efficiency," *Anal. Chem.* (1993) 65: 1481–1488.

Seiler, K. et al., "Electroosmotic Pumping and Valveless Control of Fluid Flow Within a Manifold of Capillaries on a Glass Chip," *Anal. Chem.* (1994) 66:3485–3491.

Sundberg, S. A., "High–throughput and ultra–high–throughput screening: solution—and cell– based approches," *Current Opinions in Biotechnology* 2000, 11:47–53.

* cited by examiner

MICROFLUIDIC SYSTEMS AND METHODS FOR DETERMINING MODULATOR KINETICS

CROSS-REFERENCE TO RELATED APPLICATIONS

Pursuant to 35 U.S.C. §119(e), the present application claims benefit of and priority to U.S. Ser. No. 60/142,984, entitled "Microfluidic Systems and Methods for Determining Modulator Kinetics," filed Jul. 6, 1999 by Chow et al.; and co-filed PCT application "Microfluidic Systems and Methods for Determining Modulator Kinetics," filed Jun. 30, 2000, by Chow et al.

BACKGROUND OF THE INVENTION

The determination of kinetic relationships for reactants and other components in microfluidic systems can be a relatively complex process. In this regard, the inventors and their co-workers have determined a variety of useful methods of determining kinetic information for reactions and other phenomena in such microfluidic systems. For example, "APPARATUS & METHODS FOR CORRECTING FOR VARIABLE VELOCITY IN MICROFLUIDIC SYSTEMS," WO98/56956 by Kopf-Sill et al. provides pioneering methods of obtaining kinetic information for moving reactants, based, e.g., upon the conservation of flux in microscale systems which use electrokinetic forces to move fluids.

The difficulties of determining kinetic information are compounded in high-throughput systems where thousands of test compounds per day can be screened in a single microscale system for activity on one or more selected targets. Pioneering high-throughput screening methods and relevant apparatus are described by the inventors and their co-workers in Knapp et al. "CLOSED LOOP BIOCHEMICAL ANALYZERS" (WO 98/45481; PCT/US98/06723); Parce et al. "HIGH THROUGHPUT SCREENING ASSAY SYSTEMS IN MICROSCALE FLUIDIC DEVICES" WO 98/00231 and in, e.g., No. 60/128,643, filed Apr. 4, 1999, entitled "MANIPULATION OF MICROPARTICLES IN MICROFLUIDIC SYSTEMS," by Mehta et al.

One of the rate limiting aspects of high-throughput screening in general is the need to sample and re-sample the effect of a given test reagent at a variety of concentrations to provide kinetic or other activity data, such as dose-response information. Irrelevant samples (i.e., those with little or no activity in the system of interest) are often unnecessarily re-sampled to determine whether they provide an activity of interest. The need for multiple sampling strategies effectively increases the number of sampling events that a system performs, decreasing the overall throughput of the system. Furthermore, this resampling can involve multiple xyz spatial translations of a microfluidic sample loader or sample library, or both, to provide access to samples of interest, further reducing system throughput.

Accordingly, it would be extremely useful to be able to acquire kinetic information from one or a few sampling events in a microfluidic system. The present invention provides methods, apparatus and systems for generating and deconvoluting signal information and for reduced resampling in high throughput systems (including both pressure-based and electrokinetic systems), as well as a variety of other features which will become apparent upon complete review of the following.

SUMMARY OF THE INVENTION

The present invention provides for the use of signal profile information from one or a few sampling events to produce information regarding kinetics and/or reactant concentrations in a microfluidic system. In particular, the shape of the signal profile can be deconvoluted to provide kinetic information and to provide directed re-sampling of a source of sample materials.

In one set of methods, the dwell time for a system sampler is varied to modulate the profile of a signal profile, thereby providing a basis for activity determination and for limiting the need for re-sampling by the system. The system sampler will often utilize pressure-based sampling elements (e.g., pressure-based pipettor channels), although the methods herein can also be adapted to electrokinetic and other fluid movement systems.

In other methods, the dwell time is not necessarily varied, with kinetic information resulting from the deconvolution of signal profile information. Although not necessary, microfluidic channel geometry can be used to facilitate signal deconvolution, e.g., by first dispersing the sample and then reacting the dispersed sample to produce concentration gradient dependent signal information.

For example, the present invention provides high-throughput methods of sampling fluidic materials in which a plurality of different aliquots of the fluidic material are introduced into a microfluidic cavity (typically a channel, well, chamber, reservoir or other structure of microscale dimensions). These aliquots (which typically include a test material to be assayed for activity on a selected target) are produced by systematically varying dwell time at a source of the fluidic material for a microfluidic sample loader which is fluidly coupled to the microfluidic cavity, or by systematically varying a volume of the material in each aliquot. For example, the percent modulation versus target reagent concentration time can be determined by systematically varying the dwell time for a microfluidic sample loader loading material from a source of a test reagent.

The microfluidic sample loader can be configured in a variety of ways, e.g., as a fluid pressure modulatory channel, an electrokinetic modulatory channel, an electrokinetic controller, a fluid pressure controller (e.g., a vacuum source), or the like. Following loading of a test material into the system by the microfluidic sample loader, the material can be flowed into contact with target compositions in the microfluidic cavity for typical mixing reactions, e.g., with a target material.

The system is particularly useful for examining potential activity modulators (i.e., compounds or compositions which facilitate (activate) or inhibit (repress) a reaction of interest, or between an interaction between two or more moieties which interact to produce a detectable result. Typically, the modulator modulates an activity between one or more reactant and one or more reactant substrate. For example, the target composition or the test composition can include an enzyme or other catalyst, a substrate and/or an activity modulator (it will be appreciated that, e.g., kinetic activity can be determined by varying any one or all of these components, depending on the format of the reaction at issue). For example, the modulator can inhibit (e.g., as a competitive inhibitor) or enhance essentially any reaction conducted in the microfluidic system. In the methods herein, it is typical to measure a signal produced by at least one test composition, a target composition, a reaction modulator, and, an interaction between any of these components. Signals are generally produced by one or more labels in the system, and can be a component of, or released by, a reaction.

Label is typically initially confined in a region $-h<x<h$, as a function of time (t) and spatial position (x) with respect to the peak center (x=0) and the concentration (C) of the label, or of a component corresponding to the label, is equal to ½ $C_0 \{erf[(h-x)/(2Dt)^{1/2}]\}$, where $C_0$ is the initial concentration at time t=0, erf is an error function, and D is a coefficient of overall dispersion. D is equal to the sum of thermal diffusion and Taylor dispersion ($D_T$) in the system. In turn, the Taylor dispersion ($D_T$) is dependent on the dimensions and shape of the microfluidic cavity through which the label is flowed, the flow velocity (u) and the thermal diffusivity (D). Typically, $D=K(d^2u^2)/D$, where K is a proportionality factor which is a function of the microfluidic cavity through which the label is flowed and d is a characteristic microfluidic cavity length. For example, where the microfluidic cavity is a circular channel and K=1/192, d is the diameter of the circular channel and $D=D+D_T$.

In the methods herein, a kinetic rate constant is typically determined for a reaction between at least one test reagent and a target reagent. For example, the kinetic rate constant can be determined by establishing a calibration curve relating dwell time to dilution factor using one or more dye with a molecular weight which is similar to the molecular weight of the reaction modulator. For example, where the target composition is an enzyme and the test composition is an enzyme substrate, or a potential enzyme substrate, the method can include contacting the at least one test composition or the target composition with a reaction modulator, and determining a rate constant for a reaction between the enzyme or enzyme substrate in the presence of the reaction modulator. For example, the method can include determining a kinetic rate constant for a reaction between the at least one test reagent and the target reagent after exposure of the at least one test reagent, or the target reagent, or both the at least one test reagent and the target reagent, to a reaction modulator, which modulator modulates the reaction.

In a typical format, the modulator is an inhibitor such as a competitive or uncompetitive inhibitor of a reaction between the enzyme substrate or a potential enzyme substrate and an enzyme. For example, where the kinetic rate constant is for an inhibition kinetic rate constant for a competitive inhibitor ($K_I$), the reaction rate (V) is equal to $[E]_0[S]k_{cat}/([S]+K_m(1+[I]/K_I)$, where $[E]_0$ is an initial enzyme concentration, [S] is the enzyme substrate, or the potential enzyme substrate concentration, $k_{cat}$ is a measure of the enzyme turnover rate, $K_m$ is the concentration of the enzyme substrate, or the potential enzyme substrate at which V is ½ of a maximum reaction rate and [I] is the concentration of the competitive inhibitor. Relationships where the modulator is an activator, or an "uncompetitive" or "noncompetitive" inhibitor are also set forth herein.

The library of test reagents (or "modulator targets") can be configured in any of a variety of ways. For example, the library can include one or more multiwell plates comprising a plurality of test reagents. Similarly, the library can be present on the microfluidic substrate, e.g., as in a plurality of wells, reservoirs or chambers fluidly coupled to one or more microscale channel in the body of the device. In this format, the one or more wells, reservoirs or chambers collectively or individually include a plurality of test reagents. In another embodiment, the library exists on a solid support that has a plurality of dried or fixed test reagents dried or fixed to the support (in this format, microfluidic systems optionally comprise resolubilization pipettors which are fluidly coupled to other channels in the system). Other formats for library storage such as the use of microfluidic bead arrays and the like can also be used.

Typically, the microscale cavity includes a microfluidic channel. The aliquot of material (which includes a test reagent or control reagents) is typically moved through the microfluidic channel under pressure (although electrokinetic approaches are also useful). In this system, the aliquot includes a test reagent which is dispersed along a length of the aliquot in the channel by thermal diffusion and Taylor dispersion, thereby providing a Gaussian concentration profile for the test reagent. The concentration and distribution of concentration of a test reagent in a series or set of aliquots can be in any of a number of formats. For example, the center of each aliquot can be approximately the same, with the concentration of a test reagent at an edge of each aliquot being varied. Alternately, concentration of a test reagent at a center of each aliquot can be variable. The volume of a plurality of the aliquots can vary systematically along a length of the microfluidic cavity (e.g., along a microfluidic channel).

Similarly, the intensity of a signal (produced, e.g., by a detectable label) associated with some component of the aliquot (or another fluidic material) van be varied along a dimension of the microfluidic cavity as the fluidic material is flowed through the cavity. In one aspect, a plurality of signal profiles from a plurality of fluidic materials are collected to produce a library of signal profiles which can be used to deconvolute kinetic and concentration information from signals produced from known or unknown samples. For example, the library of signal profiles can include a set of look-up tables for the concentration of a modulator, reactant, catalyst, enzyme, or other moiety of interest.

In one class of embodiments, the profile of a signal is used to calculate kinetic or quantitative information by comparing the profile (produced by a reaction, e.g., in the presence of a reaction modulator), to a library of signal profiles. Comparison of the profile of the signal produced by the reaction to the library of signal profiles provides an indication of an effect of, e.g., the modulator, on a kinetic measurement of the reaction or an indication of the amount of a starting material in a reaction. Comparison of the profile of the signal produced by the reaction to the library of signal profiles is typically performed by least square analysis.

Commonly, a fluidic material of interest has an associated signal produced by a detectable label, with the intensity of the signal varying along a dimension of a microfluidic cavity (e.g., a microchannel) as the fluidic material is flowed through the cavity. One way of determining concentration and kinetic data for a reaction modulator from a profile of the signal in the cavity includes iterative estimation of an effect caused by the modulator. For example, an estimated effect of the modulator is compared to a measured effect of the modulator, with the effect of the modulator being re-estimated at the same or a different concentration, with the second estimation of the modulator being compared to the same or a different measured effect of the modulator. Estimations can be iteratively repeated and compared to measured effects of the modulator at the same or additional different concentrations on the reaction. As additional data is acquired, estimations become progressively more accurate and the concentration and kinetic information for the modulator is determined.

The present invention is especially adapted to provide high-throughput methods of determining an activity of a test material in a microfluidic system. In this preferred class of embodiments, a plurality of test materials are sampled from a test material library which includes a plurality of sources of test materials. The sampling includes introducing the plurality of test materials into a microfluidic system with a microfluidic sample loader and mixing the test materials with at least one target material in the microfluidic system.

An effect of at least one of the plurality of test materials on the target material is measured and a source of the at least one test material within the plurality of sources of test materials is determined. The source of the at least one test material in the test material library is re-sampled by varying the dwell time of the microfluidic sample loader. Typically, a plurality of aliquots of the test reagent are contacted to the target, with a plurality of signals which result from contacting the test reagent and the target being measured.

Similarly, the invention provides methods of deconvoluting concentration dependent information. In these methods, a first reagent having a dispersed concentration profile is flowed in a first channel. The first reagent is reacted with a second reagent which modulates the activity of the first reagent. A signal produced by the resulting activity of the first reagent is detected, along with a signal profile of the signal. The signal profile is then converted into a concentration-dependent activity of the first reagent.

For example, a library of signal profiles produced by mixing the first or second reagent at known or calculated concentrations with the first, second or a third reagent can be provided. The shape of any unknown signal profile is converted into a concentration-dependent activity of the first reagent by comparison of the signal to the library of signal profiles. Alternately, a value for the effect of the second reagent on the activity of the first reagent can be estimated and the estimated value compared to a measured value for the activity of the second reagent on the first reagent. This process can be reiteratively repeated to provide progressively closer approximations of concentration or kinetic information for any of the components in the system.

In other embodiments, concentration and/or signal profiles, created as described above, are used to provide quantitative information regarding starting reactants. For example, an amount of starting nucleic acid is determined in a PCR reaction by flowing the starting material through a microfluidic channel and measuring the diffusion/dispersion profile of the sample plug, e.g., during the reaction, to provide the amount of starting material.

Integrated systems and devices for practicing the above methods are also provided. For example integrated systems for sampling test reagents and determining concentration-dependent reaction information for the effect of the test reagent on a selected target reagent are provided. The apparatus includes a body having a microfluidic cavity disposed therein. A source of a plurality of test reagents is fluidly coupled to the microscale cavity (and can be internal or external to the body structure), e.g., through a pipettor channel (which can be a pressure-pipettor or an electrokinetic pipettor). A source of at least one target reagent is also fluidly coupled to the microscale cavity. One or more microfluidic conduits (typically microscale channels) are located between the microfluidic cavity, the source of a plurality of test reagents and the source of at least one target reagent. A test reagent sampler is placed in fluidic contact with the one or more microfluidic conduit. One or more computer is operably linked to the test reagent sampler. In a typical configuration, the system includes one or more libraries of potential modulator compounds, a source of an enzyme, a source of a substrate, sources of relevant buffers, and appropriate interconnecting microscale channel networks.

The computer typically includes software relevant to practicing the methods noted above. For example, the software includes a first instruction set controlling the test reagent sampler and directing the test reagent sampler to flow a test reagent from the source of test reagents into the microscale cavity, as well as a second instruction set directing the test reagents into contact with the at least one target reagent in the microscale cavity. A third instruction set controls detection of a signal resulting from contacting the test reagent and the at least one target reagent while a fourth instruction set directs varying dwell time of the test reagent sampler in contact with the source of test reagent and/or varying the volume of a test reagent sample loaded by the test reagent sampler. A fifth instruction set directs resampling of the source of test reagents by the test reagent sampler (optionally, the fifth instruction set is executed by the integrated system concurrent with the fourth instruction set).

A detector monitors the signal produced by contacting the test reagents and the at east one target reagent during operation of the system. Typically, the detector is operably linked to the at least one computer, which also includes signal deconvolution software for converting a detected signal profile into concentration-dependent test reagent-target reagent reaction information, e.g., by calculating any of the relationships for concentration or kinetic information noted above. Similarly, the signal deconvolution software optionally includes an instruction set for comparing a detected signal profile resulting from contacting the test reagent and the at least one target reagent to a library of signal profiles produced by mixing the test or target reagent at known or calculated concentrations with the test, target or an additional reagent. As noted above, the shape of the signal profile is converted into a concentration-dependent activity of the first reagent by comparison of the detected signal profile to the library of signal profiles. The signal deconvolution software optionally includes an instruction set for comparing and estimating a value for the effect of the test reagent on the activity of the target reagent and for comparing the estimated value to a measured value for the activity of the test reagent on the target reagent. The signal deconvolution software optionally includes an instruction set for reiteratively estimating values for the effect of the test reagent on the activity of the target reagent at different concentrations or introduced fluid volumes of the test or target reagent and for comparing the estimated values to measured values for the activity of the test reagent on the target reagent at the different concentrations or introduced volumes. In this embodiment, after each measurement of activity at each concentration or introduced volume of test and target reagent, the measured information is used to refine an estimated value of an effect by the test reagent on the activity of the target reagent at an additional concentration.

DETAILED DESCRIPTION OF THE INVENTION

Figure 1:
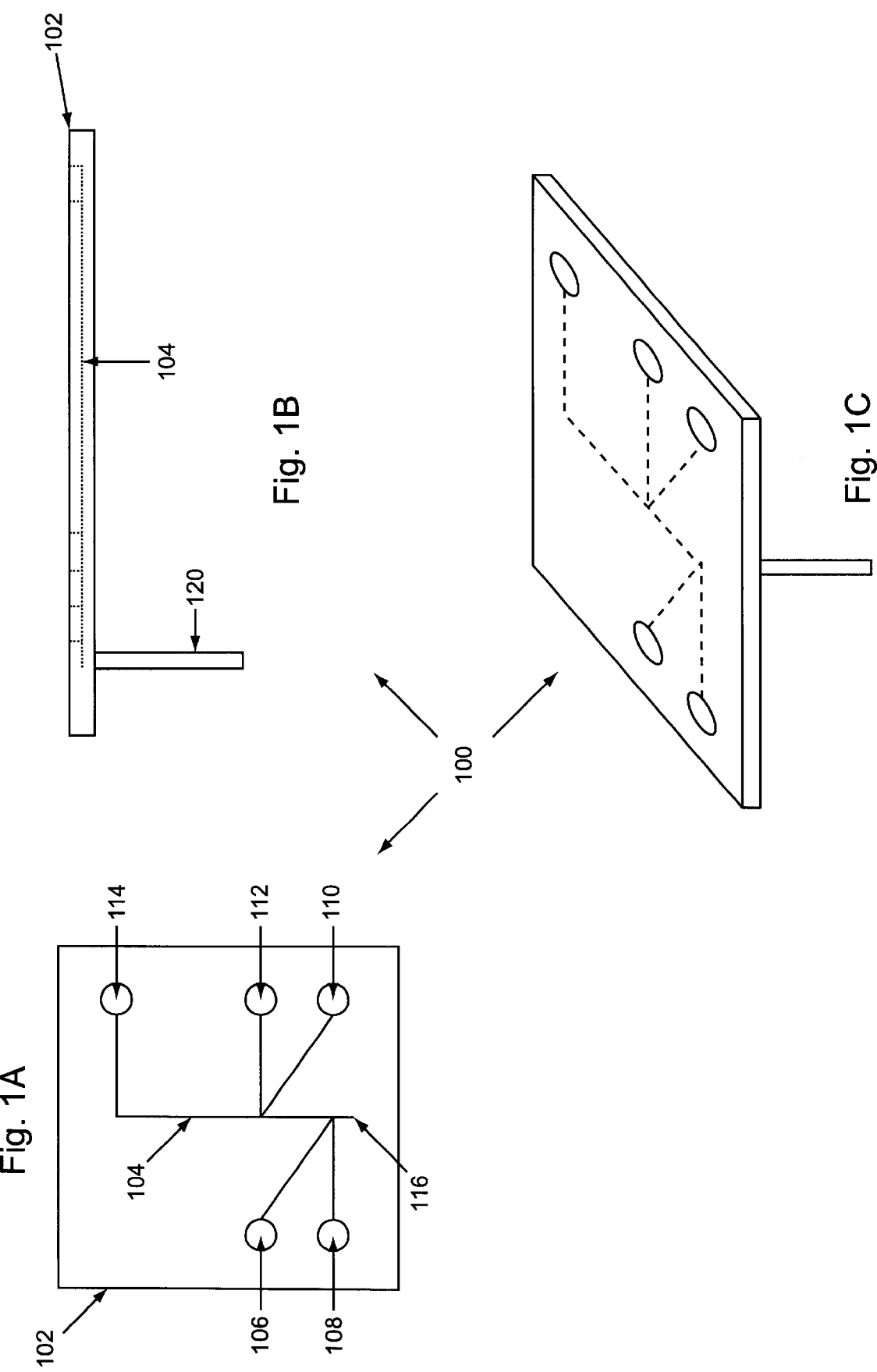
FIG. 1, panels A, B and C are schematic drawings of an integrated system of the invention, including a body structure, microfabricated elements, and a pipettor channel.

The determination of kinetic rate constants provides a measure of activity for two or more reactants. This measure of activity is useful in monitoring chemical and biological interactions, e.g., in product screening assays.

The present invention provides new strategies for determining kinetic rate constants in microscale systems. In particular, kinetic rate constants are determined by examining signal profile information which results from sampling of reaction components by the microfluidic system and flowing of the reaction components within the system. Signal profiles are also optionally used to provide quantitative information, e.g., to perform quantitative PCR in one step. Signal profile information can also be controlled, thereby facilitating kinetic determinations, e.g., by varying sample dwell time for a material sampler connected to or incorporated into the system. Control of profile information can also be achieved by varying channel geometries to produce dispersed samples for reaction and analysis.

Determination of rate constants for reaction modulators, such as inhibition rate constants ($K_I$) or activation rate constants ($K_A$), is performed by determining the relation of the percentage inhibition or activation concentration for a given enzyme/catalyst and substrate/reactant concentration (i.e., in the presence of the relevant modulator). Other reactants and products are also assessed by these methods, including ligand and ligand binders such as an antibody and an antibody ligand, a receptor and a receptor ligand, biotin and avidin, proteins and complementary binding proteins, carbohydrates and carbohydrate binding moieties, nucleic acids, etc. Reactions which are monitored can be "fluorogenic or non-fluorogenic. Multiple reactants and products are optionally assessed by serial or simultaneous detection methods, or a combination thereof.

In high throughput screening using a microfluidic system, reagents comprising candidate modulators are usually prepared in or on microtiter plates or solid substrates or other library composition storage formats at one or a few given concentration(s) per potential modulator. After a primary screen at high throughput to identify reagents that comprise relevant modulators, one common strategy is to prepare another microtiter plate or substrate comprising the identified active reagents at additional concentrations to determine concentration dependence of percent modulation (inhibition or activation), e.g., using an additional microfluidic element or station. In contrast, the present invention provides, e.g., methods of using a single source of potential reagent modulators to determine such kinetic information, without the need for additional microtiter plates or substrate preparation steps, and without the need for multiple screening stations or microfluidic device elements.

VARYING MODULATOR OR REACTANT/SUBSTRATE CONCENTRATION

Although generally described below in terms of varying modulator concentration to provide kinetic information, it will be entirely apparent that the same kinetic information can be obtained by varying reactant concentrations, e.g., by varying the concentration of an enzyme substrate or other reactant in the system. For example, varying dwell time of a substrate sampling element at a source of substrate or otherwise varying the concentration profile of a substrate in a channel provides concentration dependent information essentially similar to that provided by varying modulator concentration by varying the concentration of modulator in a channel. Similarly, both reactant and modulator concentrations can be simultaneously varied. Consideration of the kinetic relationships noted herein shows that reactant and/or modulator information can be varied to provide kinetic information.

KINETIC DETERMINATION INCLUDING BY VARYING DWELL TIMES AT A SAMPLE SOURCE

In a first set of related methods, real time analysis of high throughput screening (HTS) data can immediately identify active compositions (modulators, inhibitors, compounds, etc.). While screening a plate or other library substrate, the microfluidic system will be directed to access wells in the plate or positions on the substrate to perform additional analysis of the active composition (i.e., by repetitively sampling the source of a composition of interest. In general, it is now discovered that the maximum concentration of a sample band is monotonically related to sample dwell time, whether using electrokinetic or pressure driven flow to access the sample. Thus, the percent inhibition versus sample concentration curve can be obtained simply by scanning a range of sample dwell times from a single sample source. This sampling procedure eliminates the need for repeatedly moving a sampling system into contact with a sample source during an initial sample screen. Two general approaches (calibration and calculation) are described in more detail below.

To establish a calibration curve relating dwell time to dilution, an easily detectable labeled moiety, such as a dye, with a molecular weight comparable to the molecular weight of a compound to be screened is used to establish a calibration curve. The calibration curve is then used to determine the concentration of a modulator compound, as a function of the time that the microfluidic system accesses ("sips") the potential activity modulator from a source of modulator compounds. Relevant kinetic constants can be determined as a function of dwell or "sip" time from the appropriate kinetic relationships for the relevant reaction mechanism.

In general, the Michaelis-Menten equation specifies that the velocity of an enzyme-substrate reaction following the conditions $$E + S \underset{k_2}{\overset{k_1}{\rightleftarrows}} ES \overset{k_3}{\rightarrow} E + P,$$

(V) is equal to

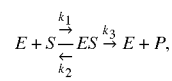

$$V_{max} \frac{[S]}{[S] + K_M}.$$

Thus, $K_M$ is equal to the substrate concentration in an enzyme substrate reaction at which the reaction rate is equal to ½ its maximal value. The Michaelis constant $K_M$ and the maximal rate for a reaction in the absence of modulator can readily be derived from rates of catalysis at different substrate concentrations, if an enzyme operates according to a standard simple reaction scheme noted above. For example, it is convenient to transform the Michaelis-Menten equation into one that gives a straight line plot, i.e., $$\frac{1}{V} = \frac{1}{V_{max}} + \frac{K_M}{V_{max}} \cdot \frac{1}{[S]}.$$

A plot of 1/V versus 1/[S] yields a straight line with an intercept of $1/V_{max}$.

In one aspect, the modulators of the invention reversibly or irreversibly inhibit the reaction under consideration. A competitive inhibitor typically binds to an enzyme or catalyst at the same site as a substrate or reactant in the reaction:

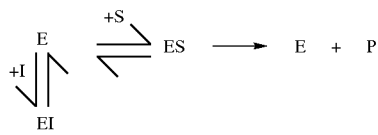

A non-competitive inhibitor diminishes the rate of catalysis by the enzyme or substrate by reducing the proportion of enzyme molecules that have a substrate bound in a functional active site on the enzyme or catalyst, without binding to the same site on the enzyme:

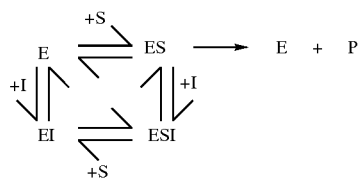

An indication that an inhibitor is a competitive inhibitor is that the inhibition is overcome by a sufficiently high concentration of substrate. In contrast, for non-competitive inhibition, the inhibitory effect is not overcome by increasing the substrate concentration.

For a competitive enzyme inhibition reaction (i.e., where the modulator is a competitive inhibitor for a given enzyme) obeying Michaelis-Menten kinetics noted above, the reaction rate (V) can be described by the equation: $V=[E]_0[S] k_{cat}/([S]+K_m(1+[I]/K_I)$. In this equation, $[E]_0$ is an initial enzyme concentration (usually known in the microfluidic system at issue, i.e., the concentration at a source of enzyme accessed by, or part of, the microfluidic system where any mixing of components is performed). [S] is a substrate concentration (again, this is usually known in the system, and is the concentration at a source of enzyme accessed by, or part of, the microfluidic system where any mixing of components is performed). $K_{cat}$ is the turnover number, $K_m$ is the concentration of substrate at which V is half the maximum reaction rate and [I] is the concentration of inhibitor. Competitive relationships are often expressed for convenience as a reciprocal plot for $1/V$, e.g., $1/V=1/V_{max}+1/V_{max}(1+[I]/K_I)(1/[S])$. In other words, the slope of the plot is increased by the factor $(1+[I]/K_I)$ in the presence of the competitive inhibitor.

For non-competitive and uncompetitive inhibition reactions, analogous equations describing $K_I$ can be substituted. In non-competitive inhibition, $V_{max}$ is decreased and so the intercept of the Y axis of a plot of $1/V$ versus $1/[S]$ is increased. The slope of the plot, which is equal to $K_M$ is not significantly affected in non-competitive inhibition. For example, in a non-competitive inhibition reaction in which the inhibitory effect is not significantly altered by the concentration of substrate in the system, $V^I_{max}=V_{max}/(1+[I]/K_I)$. In this equation, $V^I_{max}$ is the maximal velocity of the reaction in the presence of a selected concentration of non-competitive inhibitor.

One of skill will, of course, recognize that many enzymes do not exhibit Michaelis-Menten kinetics. For example, allosteric enzymes display sigmoidal plots of reaction velocity versus substrate concentration (as opposed to hyperbolic for Michaelis-Menten kinetics). For example, an allosteric enzyme can exist in two conformations, e.g., an "R" or "relaxed" confirmation which has a high affinity for a substrate (S) and a "T" or "tense" confirmation which has a low affinity for S (e.g., as per the classic Monod-Wyman-Changeux allosteric transition model e.g., in Monod et al. (1965) *J. Mol. Biol.* 12:88–118). In this case, the [occupied sites]/the [total sites=Y, which equals $$\left(\frac{[S]}{K_R}\right)\frac{1+[S]/K_R}{L+(1+[S]/K_R)^2},$$

where $K_R=2[R_0][S]/[R_1]$, $R_0$ is the relaxed form in absence of substrate, To is the tense form in the absence of substrate and L=the ratio of the concentration of $T_0/R_0$. Similarly, $V=YV_{max}$. Hence, the proportion of enzyme molecules in the R form increase progressively as more substrate is added and the binding of substrate is cooperative.

In the case of an allosteric enzyme, an allosteric inhibitor preferentially binds to the T form, while an allosteric activator preferentially binds to the R form of the enzyme. Consequently, an allosteric inhibitor shifts the R⇌T conformational equilibrium towards the T form of the enzyme, while an allosteric activator shifts the R⇌T conformational equilibrium towards the R form of the enzyme.

Allosteric interactions can also be modeled by the classic "sequential model" of Koshland (see, Koshland et al. (1966) *Biochemistry* 5:365–385). In this model, there are two confirmational states accessible by any one subunit of the enzyme. The binding of a substrate changes the shape of the enzyme subunit to which it is bound. However, the conformations of the other subunits of the enzyme are not appreciably altered. The conformational change elicited by binding of substrate in one subunit can increase or decrease the substrate-binding affinity of the other subunits in the same enzyme molecule. Alterations in substrate binding sites are sequential in this model rather than concerted as in the Monod-Wyman-Changeux model.

Which model most accurately reflects the binding interaction of a given enzyme is determined empirically, i.e., by measuring observed results against the values for activity predicted by a given model.

DECONVOLUTION METHODS USING CONCENTRATION PROFILING

In a second related set of methods, concentration dependence information is deconvoluted directly from the shape of a signal profile resulting from incubation of a modulator with other components of a microfluidic system. For example, in a pressure-driven flow system, the sample band disperses from a relatively narrow and sharp peak mainly by thermal diffusion and Taylor dispersion as the sample travels along a channel, i.e., due to the parabolic flow profile of the sample in the channel. Consequently, the modulator sample band contains a spectrum of concentration information in a single dispersed sample profile. Thus, one can use either calibration by a tracer dye or by first principle calculations (or by both means) to determine the deconvolution function (s) used to extract the percentage inhibition versus concentration information from the modification in signal profile caused by the modulator. As with the preceding method, this approach can also be used to extract competition kinetics of competition binding assays in a high-throughput format.

The concentration distribution (C) of a substance initially confined in a region $-h<x<+h$ as a function of time (t) and spatial position (x) with respect to the peak center (x=0) can be described by the relationship:

$$C = \tfrac{1}{2} C_0 \{erf[(h-x)/(2(Dt)^{1/2}] + erf[(h-x/(2(Dt)^{1/2})]\}.$$

In this equation, $C_0$ is the initial concentration at time t=0, erf is an error function, and D is the coefficient of dispersion. The dispersion coefficient D is the sum of dispersion due to thermal diffusion and Taylor dispersion. The Taylor dispersion coefficient ($D_T$) is in turn a function of the flow geometry, flow velocity (u) and the thermal diffusivity (D): $D_T = K(d^2 u^2)/D$, where K is a proportionality factor which is characteristic of a microfluidic cavity cross-section geometry (e.g., the geometry of a microscale channel) and d is the characteristic channel length. In the case of a circular channel, K=1/192 and d is the diameter. The total dispersion in this case is, therefore, $D=D+D_T$. In the case where only the concentration in the center of the modulator band (i.e., a region of a microscale channel which includes the modulator M) is of interest, $[M] = C_{x=0} = C_0 \{erf[h/(2(Dt)^{1/2})]\}$. The sample plug width, 2h, can be calculated from the sip time times the flow velocity. Again, an inhibition constant ($K_I$) or activation constant ($K_A$) can be determined from appropriate kinetic equations as noted above.

DECONVOLUTION METHODS FOR USING THE ENTIRE INHIBITOR CONCENTRATION PROFILE

At least two general routes for deconvoluting concentration and kinetic information from the signal profile of a signal peak in a flowing microfluidic system are provided. In a first approach, a library of "look up" tables are constructed using the concentration distribution equation of the modulator (e.g., inhibitor) noted above, along with the diffusion coefficient equations also noted above, combined with an appropriate kinetic equation as noted above, to provide different $K_I$ or $K_A$ as a function of time t and spatial position x with respect to the center of the inhibitor peak under predetermined enzyme reaction conditions of $[E]_0$ and $[S]$, and with known enzymatic constants $k_{cat}$ and $K_M$. During high-throughput screening, the measured inhibition profile of an inhibitor compound is matched, e.g., using least square or other common analysis methods, to the profiles stored in the library of look up tables for $K_I$ determination. Libraries can include measured profiles and observed kinetic and concentration information for any given enzyme substrate system, and/or calculated profiles, kinetic information and concentration data.

In a second approach, an initial estimate of $K_I$ or $K_A$ is performed and the above kinetic relationships are used to calculate an entire inhibition profile. The calculated profile is compared with a measured profile and any discrepancy is used to derive an improved estimate of $K_I$ or $K_A$. This process is iteratively repeated (generally only one or a few iterations (generally less than 5) are needed to provide an extremely close estimate of the kinetic constant at issue).

VARYING CHANNEL GEOMETRY TO PROVIDE CONCENTRATION DEPENDENT REACTION INFORMATION

Figure 3:
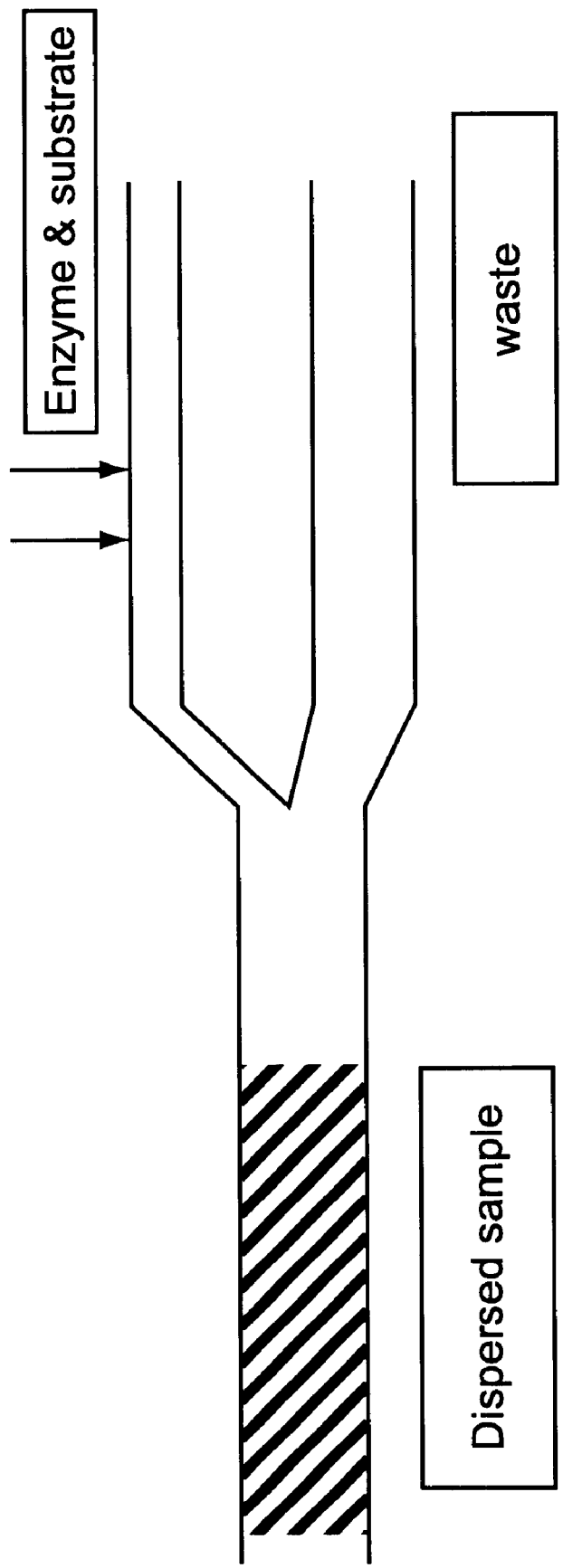
FIG. 3 is a schematic drawing of coupled diffusive and non-diffusive channels, showing channel geometry for dispersing and reacting a material to provide concentration-gradient reaction information.

In one aspect, channel geometry is varied to modulate concentration of reactants or modulators. For example, as shown in FIG. 3, a modulator (or, e.g., an enzyme substrate) can be flowed into the system (e.g., under pressure or by electrokinetic flow) in a relatively wide and/or deep channel (e.g., about 50–100 microns or larger in width, and/or 20, 50 or 100 or more microns in depth), causing dispersion of the modulator (or reactant) in the channel. In particular, the modulator (or reactant) will have a highest concentration in the center of a sample band (or "plug"), with the concentration being lower at the ends of the sample band. If this dispersed sample band is moved into contact with the additional components of the assay (e.g., an enzyme and a substrate in the situation where the band is a modulator band) in a narrower or shallower non-dispersive reaction channel, followed by detection of signal generation with a detector, the resulting signal profile will reflect a bell-shaped concentration profile of the sample band. This concentration-dependent signal profile is used as noted herein to produce kinetic information.

To keep velocity from increasing in the narrower/shallower channel, at least a second waste or analysis channel is fluidly coupled to the dispersive channel (additional reaction channels are optionally split from the dispersive channel, e.g., to provide for parallel analysis of samples/reactants). This second channel draws fluid from the dispersive channel, thereby reducing the velocity of fluid in the non-dispersive reaction channel.

In general, signal profiles are generated by detecting signal in or proximal to the first reaction channel (and or any additional reaction channels in parallel analysis embodiments noted above). In an alternate embodiment, signals from the reaction are detected by simultaneously injecting reacted materials into a plurality of side channels from the first reaction channel, thereby providing "slices" of the overall signal profile to the side channels. Signal information from these sample slices is reassembled to provide relevant concentration dependent reaction information.

VELOCITY CORRECTION IN ELECTROKINETIC SYSTEMS

Any of the movement methods herein can be used, individually or in combination, to move components through a microscale system. Most typically, pressure based systems are used to move fluids, as the calculation of kinetic information is further complicated in electrokinetic systems by the need to correct for effects of variable velocity of different components in the system. However, some assays are desirably carried out in electrokinetic systems, particularly those assays which use "non fluorogenic" assay formats. Kinases are a specific example of enzymes which catalyze reactions easily detected by non-fluorogenic methods and the detection of kinase activity and kinase activity modulators is a preferred use of the methods of the present invention.

In particular, kinases recognize specific polypeptide sequences and phosphorylate them. Phosphorylation changes the peptide charge, mass and structure, and thus the mobilities of the non-phosphorylated and phosphorylated species are different. As a consequence of this change in mobility, substrate and product move at different rates in an applied field.

In general, electrokinetic or pressure based flow mechanisms can be used to flow analytes or products in electrokinetic systems. In the present invention, pressure and hydrostatic forces will often be used alone, or in conjunction with electrokinetic control to flow modulators, reactants, products, or other components relevant to the assays herein. A special consideration relevant to the present invention is the recognition that differential velocity of charged flowing components affects kinetic and concentration calculations in systems utilizing electrokinetic flow. Several methods and systems for compensating for the effects of velocity on kinetic calculations in flowing microscale systems are set forth in detail in "APPARATUS & METHODS FOR CORRECTING FOR VARIABLE VELOCITY IN MICROFLUIDIC SYSTEMS," WO98/56956 by Kopf-Sill et al. (the '956 publication)

In brief, the concentration of products and reactants is typically measured at a selected position on the microscale fluidic device, e.g., spectrophotometrically, radioscopically, electrochemically, or optically (this applies to both pressure-based and electrokinetic systems and to systems which use both pressure and electrokinetic forces to move materials). In electrokinetic systems, velocity rates are optionally determined by measuring the speed of a component in a portion of the microscale fluidic device over time, or are determined by consideration of the parameters influencing velocity, e.g., the charge and mass of the component in an electric field. By taking advantage of the conservation of flux, the velocity of a reactant or product can be determined by measuring a different reactant or product. Thus, any or all reactants or product velocities can be observed or determined. Velocity markers are also optionally used to approximate velocity. The '956 publication also described electrokinetic devices and fluid injection schemes which self-correct for velocity effects on fluids.

In one class of embodiments, the microscale fluidic device provides for electrokinetic movement of reactants, modulators and products along a microfluidic channel. A microfluidic device incorporating an electrokinetic fluid controller is provided. An electric field is applied along a length of a microchannel, causing charged species such as reactants, solvent molecules and products to move along the length of the channel due to electrophoretic flow, as well as by bulk electroosmotic flow of the solvent in the channel. A first reaction component having a first charge mass ratio ($CM_1$) and a first velocity ($U_1$) is contacted by a second reaction component having a second charge mass ratio ($CM_2$) and a second velocity ($U_2$) in the microchannel, thereby permitting formation of a reaction product with a third charge mass ratio ($CM_p$) and a third velocity ($U_p$). This reaction can be performed in the presence or absence of a modulator. Additional reaction components and products are optionally provided and assessed for velocities and concentrations and additional modulators are, of course, also assessed where appropriate. In one embodiment, a reactant can have a velocity of zero, e.g., because it is fixed to a substrate of the detection apparatus. However, the more typical case is for flowing reactants, where all reactants, modulators, and products are flowing in channels of the system. Typically, the product has a velocity different from one or more reactants in the system.

The present invention provides methods of accurately determining the rate of a chemical or biochemical reaction. The reaction can be between two or more components that chemically join (by forming a covalent or non-covalent association) to form a new component or complex, or between a component such as an enzyme and catalyst, or an electromagnetic radiation that converts a first reactant or other component into a product, or due to spontaneous degradation of a component. The effects of modulators on any of these reactions can easily be determined using the kinetic relationships herein. In other embodiments, the present invention provides quantitative amplification, e.g., PCR, LCR, or the like, reactions. A nucleic acid template to be amplified is contacted with amplification reagents, e.g., a polymerase, and amplified; and the starting amount of nucleic acid is determined from the concentration profile of the sample.

In methods using electrokinetic flow, a first component and a second component are contacted, often by mixing, typically in a channel in an electrokinetic device. The components react to form a product. Typically, the effect of a modulator on the system is also assayed.

Flux (J), with units of molecules/(cross sectional area×time) or mass/cross sectional area×time, is equal to the velocity of the molecules under consideration (U) times the concentration of molecules (C); thus, $J=U \times C$. Flux is typically conserved in a microchannel under electrokinetic control. In other words, the number of analyte molecules (enzymes, substrates and products, or ligands and ligand partners) times the velocity of the components in a microchannel is constant along the channel.

The components and the solvent all travel along the length of the channel at different velocities to a position downstream of the mixing point where they are detected, typically by detecting a label (a variety of labels are described supra).

The velocity of one or more reaction components ($U_{r1}$, $U_{r2}$, $U_{r3}$ ...) or products ($U_{p1}$, $U_{p2}$, $U_{p3}$ ...) in the channel is determined. In a system in which flux is conserved, if the velocity of one component is known, the velocities of the other components can be determined, given concentration information, charge mass ratios (ordinarily, the charge mass ratio (CM) is proportional to velocity in a flowing system, i.e., $U_{r1}$ is proportional to $CM_{r1}$, $U_{r2}$ is proportional to $CM_{r2}$, $U_3$ is proportional to $CM_{r3}$, $U_{p1}$ is proportional to $CM_{p1}$ ...), or the like. In some unusual instances, velocity (U) and charge mass ratios (CM) are not directly proportional due to unusual molecular shapes which either shield charge on portions of the molecules, or which cause molecular drag during electrophoretic motion.

In one convenient embodiment, the velocities of the reactants are known, either from direct measurement, or from previous measurements in a similar system, or by comparison to known velocity markers. Velocity markers are components which are run in the system which are detectable and known to have a particular velocity relative to an analyte. Measurement of the marker is used to estimate the velocity of the analyte (reactant, product or the like). The product velocity may be similarly known, or directly measured, e.g., by measuring the velocity of a detectable product over a section of the microchannel. Similarly, the velocities of the reactants can be measured over a section of the microchannel.

The concentration of the reaction product is determined in a portion of the microchannel. This determination can be done by measuring the number of molecules with a detector as described herein, typically in a given section of an electrokinetic channel. Alternatively, the concentration can be determined indirectly, by measuring velocities and concentrations of other components in the system. Where flux is conserved, the sum of the concentration of reactants and products times the respective velocity of reactants and products is constant. Accordingly, the concentration of particular components can be measured, or determined from measurements for other components in the system, e.g., using simple algebra. For example, in a simple system having reactant 1 (R1) reactant 2 (R2) and a product (P) where J is constant, and $J=(U_{R1})[R_1]+(U_{r2})[R2]+(U_p)C_P$, one of skill can easily determine $C_p$ where J is constant and $J=[U_1C_1+U_2C_2+U_PC_P]_w=[U_1C_1+U_2C_2+U_PC_P]_z$. By algebraic manipulation $C_{Pz}=(U_1/U_p)(C_{1w}-C_{1z})+(U_2/U_p)(C_{2w}-C_{2z})+C_{Pw}$. Similar algebraic considerations can be used to yield the velocities or concentrations of other components where sufficient information is available. For example, the concentration of a starting reactant, e.g., in an amplification reaction, is determined. Linear algebra techniques are conveniently used to solve for the concentrations or velocities of components where there are multiple unknowns related in multiple flux relationships.

Given the velocity of a product ($U_P$) and the concentration of a product ($C_P$), it is possible to correctly determine the rate of a reaction. In particular, it is possible to determine the rate at which a product is formed, by conversion of one or more of the reactants into a product.

In the system in which one of the reactants aids in converting the other reactant into the product (e.g., where R1 is an enzyme or catalyst and R2 is a substrate), the following flux relationship can be used in determining a reaction rate: Flux $(J)=[R1] \times T_{LR2} \times k \times U_{R2} = [R2]_{converted} \times U_{R2} = U_P \times C_P$, where k is the turnover number for the enzyme reaction. Rearranging and writing transit time ($T_{LR2}$) of substrate as $L/U_{R2}$ results in: $[R1] \times L/U_{R2} \times k \times U_{R2} = U_P \times C_P$. Thus, $[R1]/U_P \times L \times k = C_P$. Substituting transit time for product ($T_{LP}$) for $L/U_P$ gives the result that product concentration is proportional to the transit time of the product, and not the substrate as might have been extrapolated from the stationary or non-mobility changing case above: $[R1] \times T_{LP} \times k = C_P$. Thus, $k = C_P/([R1]T_{LP})$. In one embodiment, where the product concentration before a reaction is zero and the enzyme concentration, R1 remains essentially constant, then, rearranging, $C_P = ([R2]_{total-[R2]unreacted}) U_2/U_P$. Consideration of the case in which two or more components are joined to form a product is similar. When two reactants join, they typically result in a product with a different velocity than either of the two individual reactants (R1 and R2). With the flux being conserved, the concentration of detected species changes as a result of a change in velocity. The product optionally results in a different detectable label than either of the reactants, or can have the same label. Where R1 and R2 molecules are converted to P, taking the principle of the conservation of flux into account: $[R1] \times U_{R1} = C_P \times U_P$ Recognition of this relationship allows quantification of the amount of R2 present in the system by detecting downstream fluorescence (all R2 is bound to R1). The relationship between the concentrations of R1 bound to R2 (i.e., forming P) and unbound R1 is proportional to their mobilities: $C_P = [R1] \times U_{R1}/U_P$.

At intermediate amounts of R2, where a portion of R1 is bound to R2, the concentration is proportional to the fraction ($Y_{R1}$) of R1 that is bound to R2: $C_P = Y_{R1} ([R1]U_{R1}/U_P)$.

It will be appreciated that products and reactants need not be "signalogenic" or "fluorogenic" (i.e., producing or quenching a signal such as a fluorescent signal), but only need to be "velocitogeneic," i.e., a reaction need only produce a detectable change in velocity of a product compared to a substrate for detection of kinetic information, e.g., in an electrokinetic system. This ability to sort signals based on the velocity of products as compared to reactants provides for the detection of multiple reactions and multiple products in a single electrokinetic device. For example, kinase enzyme assays can be analyzed in an electrokinetic system.

A mass balance on the substrate of an enzyme reaction yields: $[S]_{total} = a[S]_{converted} + (1-a) [S]_{remaining}$, where "a" is the fraction of substrate (S) that is converted to product. By definition, $[S]_{converted} = C_P$. From the conservation of flux: $C_P = [S] \times U_S/U_P$. Therefore, $[S] = a[S]U_S/U_P + (1-a)[S]$. After measuring the signal before the reaction (l.h.s.) and after the reaction (r.h.s.), it is possible to solve for "a" if the velocity of substrate and product, $U_s$ and $U_P$, are known.

In many enzyme reactions, enzyme kinetics are studied in a range in which a very small portion of substrate is converted into product; in these cases, the substrate concentration can be treated as a constant. This makes the signal change due to formation of the product relatively small. To optimize the signal to noise ratio for observation of the product, it is possible to optimize electrokinetic flow so that the product velocity is slow (or close to zero) when the substrate velocity is relatively high, or to make product velocity fast while substrate mobility is slow.

When reactions are performed on microsubstrates with electrokinetic movement of solutions, the analysis of reaction rates and product formation is done from a starting point of conservation of flux. This is in contradistinction from systems in which the velocities of reactants and products do not differ, permitting analysis from a simple standpoint of concentration balance. The present invention, therefore, provides for correct determination of reaction rates, a wider range of detectable reagents (e.g., velocitogenic, rather than "signalogenic" e.g., fluorogenic), as well as simpler movement and detection apparatus. A variety of fluorogenic and non-fluorogenic assay formats are set forth in "APPARATUS & METHODS FOR CORRECTING FOR VARIABLE VELOCITY IN MICROFLUIDIC SYSTEMS," W098/56956 by Kopf-Sill et al.

FLOW OF MODULATORS, AND TARGET COMPONENTS IN MICROSCALE SYSTEMS

A variety of microscale systems which can be adapted to the present invention by incorporating modulator and target components and appropriate additional elements, as noted herein, are available. Microfluidic devices which can be adapted to the present invention by the addition of sources of modulator or target components are described in various PCT applications and issued U.S. Patents by the inventors and their coworkers, including U.S. Pat. Nos. 5,699,157 (J. Wallace Parce) issued Dec. 16, 1997, 5,779,868 (J. Wallace Parce et al.) issued Jul. 14, 1998, 5,800,690 (Calvin Y. H. Chow et al.) issued Sep. 1, 1998, and 5,842,787 (Anne R. Kopf-Sill et al.) issued Dec. 1, 1998; and published PCT applications, such as, WO 98/00231, WO 98/00705, WO 98/00707, WO 98/02728, WO 98/05424, WO 98/22811, WO 98/45481, WO 98/45929, WO 98/46438, and WO 98/49548.

For example, pioneering technology providing high-throughput microscale assays are set forth in Parce et al. "High Throughput Screening Assay Systems in Microscale Fluidic Devices" WO 98/00231 and, e.g., in 60/128,643 filed Apr. 4, 1999, entitled "Manipulation of Microparticles In Microfluidic Systems," by Mehta et al. Complete integrated systems with fluid handling, signal detection, sample storage and sample accessing are available. For example, Parce et al. "High Throughput Screening Assay Systems in Microscale Fluidic Devices" WO 98/00231 provide pioneering technology for the integration of microfluidics and sample selection and manipulation.

In general, modulators and other components can be flowed in a microscale system by electrokinetic (including either electroosmotic or electrophoretic) techniques, or using pressure-based flow mechanisms, or combinations thereof.

Pressure forces can be applied to microscale elements to achieve fluid movement using any of a variety of techniques. Fluid flow (and flow of materials suspended or solubilized within the fluid, including modulators, enzymes, enzyme substrates, catalysts, and cells or other particles) is optionally regulated by pressure based mechanisms such as those based upon fluid displacement, e.g., using a piston, pressure diaphragm, vacuum pump, probe or the like to displace liquid and raise or lower the pressure at a site in the microfluidic system. The pressure is optionally pneumatic, e.g., a pressurized gas, or uses hydraulic forces, e.g., pressurized liquid, or alternatively, uses a positive or negative displacement mechanism, i.e., a plunger fitted into a material reservoir, for forcing material through a channel or other conduit, or is a combination of such forces.

In preferred embodiments, a vacuum source is applied to a reservoir or well at one end of a channel to draw the relevant materials through the channel (e.g., fluidic compositions comprising enzymes, buffers, substrates, modulators or the like). Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357.

Hydrostatic, wicking and capillary forces can also be used to provide pressure for fluid flow of materials such as enzymes, nucleic acids, and the like. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al., Attorney Docket Number 017646-007010, U.S. Ser. No. 09/245,627, filed Feb. 5, 1999. In these methods, an adsorbent material or branched capillary structure is placed in fluidic contact with a region where pressure is applied, thereby causing fluid to move towards the adsorbent material or branched capillary structure.

It will be recognized that adsorption of assay elements such as inhibitors, activators and reactants to walls of channels of the microscale system will bias signal information, causing inaccuracies in kinetic rate calculations if this biasing is unaccounted for. Mechanisms for reducing adsorption of materials during fluid-based flow are described, e.g., in "PREVENTION OF SURFACE ADSORPTION IN MICROCHANNELS BY APPLICATION OF ELECTRIC CURRENT DURING PRESSURE-INDUCED FLOW" Ser. No. 09/310,027 filed May 11, 1999 by Parce et al. In brief, adsorbtion of potential modulators, modulator targets (enzymes, substrates, products, catalysts, cells, etc.), and other materials, such as PCR reagents, to channel walls or other microscale components during pressure-based flow can be reduced by applying an electric field such as an alternating current to the material during flow. Similarly, a variety of surface coatings are available in the microfluidic and capillary electrophoretic arts to reduce unwanted surface adsorption.

One can also determine how reactions are biased by surface adsorption, taking this surface adsorption information into account in making relevant kinetic determinations. For example, one or two or more tracer dyes with different surface adsorption characteristics can be used to determine how much of a reactant or modulator of interest is bound to a wall of a channel during an assay. For example, the signal intensity from dye(s) bound to the walls of the channel provide an estimation of how much of a reactant or modulator will be bound to the walls of the channel(s) in the system. For example, the dyes may bracket the reactant or modulator of interest in the degree to which they are adsorbed to the walls of the system, or may have some other known relationship to the properties of the reactant or modulator of interest. Alternately, alterations in the adsorption of the dye(s) to the walls can be monitored in the presence of the reactant or modulator of interest, thereby providing an adsorption kinetic relationship between the dyes and the reactant or modulator of interest.

Similarly, changes in adsorbtion over time can be monitored by monitoring the dyes.

Mechanisms for focusing materials into the center of microscale flow paths, which is useful in increasing assay throughput by regularizing flow velocity in pressure-based flow systems is described in "FOCUSING OF MICROPARTICLES IN MICROFLUIDIC SYSTEMS" by H. Garrett Wada et al., 60/134,472, filed May 17, 1999. In brief, materials are focused into the center of a channel by forcing fluid flow from opposing side channels into the main channel, or by other fluid manipulations. Diffusible materials such as the modulators of the present invention are also optionally washed from other materials, as described by Wada et al. during flow of the materials, i.e., by sequentially flowing buffer into a channel in which materials are flowed and flowing the buffer back out of the channel.

In an alternate embodiment, microfluidic systems can be incorporated into centrifuge rotor devices, which are spun in a centrifuge. Fluids and particles travel through the device due to gravitational and centripetal/centrifugal pressure forces.

One method of achieving transport or movement of modulators, modulator targets, PCR reactants, and the like through microfluidic channels is by electrokinetic material transport. "Electrokinetic material transport systems," as used herein, include systems that transport and direct materials within a microchannel and/or chamber containing structure, through the application of electrical fields to the materials, thereby causing material movement through and among the channel and/or chambers, i.e., cations will move toward a negative electrode, while anions will move toward a positive electrode. For example, movement of fluids toward or away from a cathode or anode can cause movement of transmitters, cells, modulators, etc. suspended within the fluid. Similarly, the transmitters, cells, modulators, etc. can be charged, in which case they will move toward an oppositely charged electrode (indeed, in this case, it is possible to achieve fluid flow in one direction while achieving particle flow in the opposite direction). In this embodiment, the fluid can be immobile or flowing and can comprise a matrix as in electrophoresis.

In general, electrokinetic material transport and direction systems also include those systems that rely upon the electrophoretic mobility of charged species within the electric field applied to the structure. Such systems are more particularly referred to as electrophoretic material transport systems. For electrophoretic applications, the walls of interior channels of the electrokinetic transport system are optionally charged or uncharged. Typical electrokinetic transport systems are made of glass, charged polymers, and uncharged polymers. The interior channels are optionally coated with a material which alters the surface charge of the channel.

A variety of electrokinetic controllers and systems are described, e.g., in Ramsey WO 96/04547, Parce et al. WO 98/46438 and Dubrow et al., WO 98/49548, as well as a variety of other references noted herein.

Use of electrokinetic transport to control material movement in interconnected channel structures was described, e.g., in WO 96/04547 and U.S. Pat. No. 5,858,195 to Ramsey. An exemplary controller is described in U.S. Pat. No. 5,800,690. Modulating voltages are concomitantly applied to the various reservoirs to affect a desired fluid flow characteristic, e.g., continuous or discontinuous (e.g., a regularly pulsed field causing the sample to oscillate direction of travel) flow of labeled components toward a waste reservoir. Particularly, modulation of the voltages applied at the various reservoirs can move and direct fluid flow through the interconnected channel structure of the device.

ASSAYS

In the assays of the invention, a first reactant or assay component is contacted to a second reactant or product, typically to form a product of interest. The reactants or components can be elements of essentially any assay which is adaptable to a flowing format; thus, while often described in terms of enzyme-substrate or receptor-ligand interactions, it will be understood that the reactants or components herein can comprise a moiety derived from any of a wide variety of components, including, antibodies, antigens, ligands, receptors, enzymes, enzyme substrates, amino acids, peptides, proteins, nucleosides, nucleotides, nucleic acids, fluorophores, chromophores, biotin, avidin, organic molecules, monomers, polymers, drugs, polysaccharides, lipids, liposomes, micelles, toxins, biopolymers, PCR reagents, therapeutically active compounds, molecules from biological sources, blood constituents, cells or the like. No attempt is made herein to describe how known assays utilizing these components are practiced. A wide variety of microfluidic assays are practiced using these components. See, e.g., U.S. Ser. No. 08/761,575 entitled "High Throughput Screening Assay Systems in Microscale Fluidic Devices" by Parce et al. (see also U.S. Ser. No. 08/881,696).

As used herein, the phrase "biochemical system" generally refers to a chemical interaction that involves molecules of the type generally found within living organisms or extracts derived from living organisms. Such interactions include the full range of catabolic and anabolic reactions which occur in living systems including enzymatic, binding, signaling and other reactions. Further, biochemical systems, as defined herein, also include model systems which are mimetic of a particular biochemical interaction. Examples of biochemical systems of particular interest in practicing the present invention include, e.g., receptor-ligand interactions, enzyme-substrate interactions, cellular signaling pathways, transport reactions involving model barrier systems (e.g., cells or membrane fractions) for bioavailability screening, and a variety of other general systems. Cellular or organismal viability or activity may also be screened using the methods and apparatuses of the present invention, e.g., in toxicology studies. Biological materials which are assayed include, but are not limited to, enzyme preparations, cells, cellular fractions (membranes, cytosol preparations, etc.), agonists and antagonists of cell membrane receptors (e.g., cell receptor-ligand interactions such as e.g., transferrin, c-kit, viral receptor ligands (e.g., CD4-HIV), cytokine receptors, chemokine receptors, interleukin receptors, immunoglobulin receptors and antibodies, the cadherein family, the integrin family, the selectin family, and the like; see, e.g., Pigott and Power (1993) *The Adhesion Molecule FactsBook* Academic Press New York and Hulme (ed) *Receptor Ligand Interactions A Practical Approach* Rickwood and Hames (series editors) IRL Press at Oxford Press NY), toxins and venoms, viral epitopes, hormones (e.g., opiates, steroids, etc.), intracellular receptors (e.g. which mediate the effects of various small ligands, including steroids, thyroid hormone, retinoids and vitamin D; for reviews see, e.g., Evans (1988) *Science*, 240:889–895; Ham and Parker (1989) *Curr. Opin. Cell Biol.*, 1:503–511; Burnstein et al. (1989), *Ann. Rev. Physiol.*, 51:683–699; Truss and Beato (1993) *Endocr. Rev.*, 14:459–479), peptides, retro-inverso peptides, polymers of $\alpha$-, $\beta$-, or $\omega$-amino acids (D- or L-), enzymes, enzyme substrates, cofactors, drugs, lectins, sugars, nucleic acids (both linear and cyclic polymer configurations), oligosaccharides, proteins, phospholipids and antibodies. Synthetic polymers such as hetero-polymers in which a known drug is covalently bound to any of the above, such as poly-urethanes, polyesters, polycarbonates, polyureas, polyamides, polyethyleneimines, polyarylene sulfides, polysiloxanes, polyimides, and polyacetates are also assayed. Other polymers are also assayed using the systems described herein, as would be apparent to one of skill upon review of this disclosure.

One of skill will be generally familiar with biological literature. For a general introduction to biological systems, including enzymes, see, Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook); *Current Protocols in Molecular Biology*, F. M. Ausubel et al., eds., Current Protocols, a joint venture between Greene Publishing Associates, Inc. and John Wiley & Sons, Inc., (through 1998 Supplement) (Ausubel); Watson et al. (1987) *Molecular Biology of the Gene, Fourth Edition* The Benjamin/Cummings Publishing Co., Menlo Park, CA; Watson et al. (1992) Recombinant DNA Second Edition Scientific American Books, NY; Alberts et al. (1989) *Molecular Biology of the Cell Second Edition* Garland Publishing, NY; Pattison (1994) *Principles and Practice of Clinical Virology*; Darnell et al., (1990) *Molecular Cell Biology second edition*, Scientific American Books, W. H. Freeman and Company; Berkow (ed.) *The Merck Manual of Diagnosis and Therapy*, Merck & Co., Rahway, N.J.; *Harrison's Principles of Internal Medicine*, Thirteenth Edition, Isselbacher et al. (eds). (1994) Lewin *Genes*, 5th Ed., Oxford University Press (1994); The "Practical Approach" Series of Books (Rickwood and Hames (series eds.) by IRL Press at Oxford University Press, NY; and The "FactsBook Series" of books from Academic Press, NY.

Product information from manufacturers of biological reagents and experimental equipment also provide information useful in assaying biological systems. Such manufacturers include, e.g., the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill. In addition, an enormous amount of information regarding bioogical systems is found on the internet.

In order to provide methods and devices for screening potential modulators for effects on biochemical systems, the present invention generally incorporates model in vitro systems which mimic a given biochemical system in vivo for which effector compounds are desired. The range of systems against which compounds can be screened and for which effector compounds are desired, is extensive. For example, potential modulators are optionally screened for effects in blocking, slowing or otherwise inhibiting key events associated with biochemical systems whose effect is undesirable. As described supra, the full range of kinetic information for such systems is easily determined using the methods herein.

For example, potential modulator compounds are optionally screened for their ability to block systems that are responsible, at least in part, for the onset of disease or for the occurrence of particular symptoms of diseases, including, e.g., hereditary diseases, cancer, bacterial or viral infections and the like. Potential modulators which show promising results in these screening assay methods can then be subjected to further testing to identify whether they are suitable as effective pharmacological agents for the treatment of disease or symptoms of a disease, or for other purposes (e.g., use as industrial enzymes). Using the data correction methods described herein, the effects of assay compounds on biochemical systems is properly determined. For example, the binding properties of a test molecule to a target, or the effects of an enzyme modulator are easily determined using the methods herein.

Alternatively, modulator compositions can be screened for their ability to stimulate, enhance or otherwise induce biochemical systems whose function is believed to be desirable, e.g., to remedy existing deficiencies in a patient. Furthermore, as described extensively supra, enzyme activity levels (which can be diagnostic of diseases) are correctly determined using the methods herein.

Once a model system is selected, batteries of test compounds can be applied against these model systems. By identifying those test compounds that have an effect on the particular biochemical system, in vitro, one can identify potential effectors of that system, in vivo.

In one form, the biochemical system models employed in the methods and apparatuses of the present invention will screen for an effect of a potential activity modulator on an interaction between two or more components of a biochemical system, e.g., receptor-ligand interaction, enzyme-substrate interaction, and the like. In this form, the biochemical system model will typically include the two normally interacting components of the system for which an effector is sought, e.g., the receptor and its ligand or the enzyme and its substrate.

Determining whether a test compound has an effect on this interaction then involves contacting the system with an assay compound and assaying for the functioning of the system, e.g., receptor-ligand binding or substrate turnover/conversion to product. The assayed function is optionally compared to a control, e.g., the same reaction in the absence of the test modulator composition or in the presence of a known modulator/effector, e.g., by varying dwell time for sample loading, and/or taking proper steps to correct for velocity of components in the assay as described supra.

Typically, such assays involve the measurement of a parameter of the biochemical system. By "parameter of the biochemical system" is meant some measurable evidence of the system's functioning, e.g., the presence or absence of a labeled group or a change in molecular weight (e.g., in binding reactions, transport screens), the presence or absence of a reaction product or substrate (in substrate turnover measurements), or an alteration in electrophoretic mobility (detected, e.g., by a change in signal from a detector in the system).

Monitoring reaction rates between enzymes and substrates has applicability as a general laboratory tool for basic research, where the reaction rate is unknown, and as a quality control tool for the assessment of the quality of reagents such as enzymes or substrates. Enzymes and other chemical and biological catalysts are in common use as components of foods, food supplements, detergents, therapeutics, and, e.g., as laboratory tools for recombinant nucleic acid manipulation. See, Berger, Sambrook, and Ausubel, supra., for a discussion of some enzymes commonly used in molecular biology. Defective enzymes also serve as the direct cause for the etiology of many inherited diseases, including, e.g., ADA and phenylketonuria. The ability to screen enzymes rapidly from patients suffering enzyme defects is also of considerable medical diagnostic value.

In addition to kinase assays, a variety of other enzyme-substrate interactions are of considerable commercial and medical interest. Many enzymes and their substrates are commercially available e.g., from the Sigma Chemical Co. (Saint Louis, Mo.), the INDOFINE Chemical Company, Inc. (Somerville, N.J.); R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, WI), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill. Exemplar enzymes and assay systems which are adapted to the present invention using the methods described herein include those found in the professional literature such as those in the references above and in Passonneau and Lowry (1993) *Enzymatic Analysis: a Practical Guide* Human Press Towata N.J.; Eisenthal and Danson (1992) *Enzyme Assays: a Practical Approach* Oxford University Press, Oxford England; Deshpande (1996) *Enzyme Immuno Assays From Concept to Product Development* Chapman and Hall, NY.; Burell (1993) *Enzymes of Molecular Biology* Humana Press, Towata N.J.; and Engel (1996) *Enzymology Labfax* Academic Press, Inc. San Diego, Calif.

Although described in terms of two-component biochemical systems, the methods and system/apparatus herein are also used to screen for effectors of much more complex systems, where the result or end product of the system is known and assayable at some level, e.g., enzymatic pathways, cell signaling pathways and the like. Alternatively, the methods and apparatuses described herein are optionally used to screen for compounds that interact with a single component of a biochemical system, e.g., compounds that specifically bind to a particular biochemical compound, e.g., a receptor, ligand, enzyme, nucleic acid, structural macromolecule, etc. In all of these instances, the ability to correctly measure binding reactions, product production rates, assay component concentrations and the like, using the methods herein, makes the assay more predictive and representative.

Biochemical system models are also embodied in whole cell systems. For example, where one is seeking to screen test compounds for an effect on a cellular response, whole cells are optionally utilized. Modified cell systems are employed in the systems encompassed herein. For example, chimeric reporter systems are optionally employed as indicators of an effect of a test compound on a particular biochemical system. Chimeric reporter systems typically incorporate a heterogenous reporter system integrated into a signaling pathway which signals the binding of a receptor to its ligand. For example, a receptor is fused to a heterologous protein, e.g., an enzyme whose activity is readily assayable.

Activation of the receptor by ligand binding then activates the heterologous protein, which then allows for detection. Thus, the surrogate reporter system produces an event or signal which is readily detectable, thereby providing an assay for receptor/ligand binding. Examples of such chimeric reporter systems have been previously described in the art. An example is the common chloramphenicol acetyl transferase (CAT) assay.

Additionally, where one is screening for bioavailability, e.g., transport, biological barriers are optionally included. The term "biological barriers" generally refers to cellular or membranous layers within biological systems, or synthetic models thereof. Examples of such biological barriers include the epithelial and endothelial layers, e.g. vascular endothelia and the like. Additional assays for transporter function are described in Ser. No. 09/323747 "MICROSCALE ASSAY AND MICROFLUIDIC DEVICE FOR TRANSPORTER ACTIVITY" by Parce filed Jun. 1, 1999. See also, *Neurotransmitter Transporters: Structure, Function and Regulation* (1997) M. E. A Reith, ed. Human Press, Towata N.J., and the references cited therein.

Biological responses are often triggered and/or controlled by the binding of a receptor to its ligand. For example, interaction of growth factors, e.g., EGF, FGF, PDGF, etc., with their receptors stimulates a wide variety of biological responses including, e.g., cell proliferation and differentiation, activation of mediating enzymes, stimulation of messenger turnover, alterations in ion fluxes, activation of enzymes, changes in cell shape and the alteration in genetic expression levels. Accordingly, control of the interaction of the receptor and its ligand may offer control of the biological responses caused by that interaction.

Accordingly, in one aspect, the present invention will be useful in screening for, or testing the activity of, compounds that affect an interaction between a receptor molecule and its ligands. As used herein, the term "receptor" generally refers to one member of a pair of compounds which specifically recognize and bind to each other. The other member of the pair is termed a "ligand." Thus, a receptor/ligand pair may include a typical protein receptor, usually membrane associated, and its natural ligand, e.g., another protein or small molecule. Receptor/ligand pairs can include antibody/antigen binding pairs, complementary nucleic acids, nucleic acid associating proteins and their nucleic acid ligands. A large number of specifically associating biochemical compounds are well known in the art and can be utilized in practicing the present invention.

Traditionally, methods for screening for effectors of a receptor/ligand interaction have involved incubating a receptor/ligand binding pair in the presence of a test compound. The level of binding of the receptor/ligand pair is then compared to negative and/or positive controls. Where a decrease in normal binding is seen, the test compound is determined to be an inhibitor of the receptor/ligand binding. Where an increase in that binding is seen, the test compound is determined to be an enhancer or inducer of the interaction. The methods of correcting for velocity and other effects as noted herein provide for correct determination of these parameters. Typically, effectors of an enzyme's activity toward its substrate are screened by contacting the enzyme with a substrate in the presence and absence of the compound to be screened and under conditions optimal for detecting changes in the enzyme's activity. After a set time for reaction, the mixture is assayed for the presence of reaction products or a decrease in the amount of substrate. The amount of substrate that has been catalyzed is them compared to a control, i.e., enzyme contacted with substrate in the absence of test compound or presence of a known effector. As above, a compound that reduces the enzymes activity toward its substrate is termed an "inhibitor," whereas a compound that accentuates that activity is termed an "activator" or an "inducer." Again, using the methods herein, a correct determination of whether a component is an inhibitor, an inducer, or irrelevant to the system can more easily be determined.

Assay components such as modulators are optionally screened for their ability to affect a particular biochemical or chemical system. Assay components can include a wide variety of different compounds, including chemical compounds, mixtures of chemical compounds, e.g., polysaccharides, small organic or inorganic molecules, biological macromolecules, e.g., peptides, proteins, nucleic acids, or an extract made from biological materials such as bacteria, plants, fungi, or animal cells or tissues, naturally occurring or synthetic compositions. Depending upon the particular embodiment being practiced, the assay components are provided from a source of assay components, e.g., injected, free in solution, optionally attached to a carrier, a solid support, e.g., beads or the like. A number of suitable supports are employed for immobilization of the assay components. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, glass beads, polyaminemethylvinylether maleic acid copolymer, amino acid copolymer, ethylene-maleic acid copolymer, nylon, silk, etc. Additionally, for the methods and apparatuses described herein, test compounds are screened individually, or in groups. Group screening is particularly useful where hit rates for effective test compounds are expected to be low such that one would not expect more than one positive result for a given group. Alternatively, such group screening is used where the effects of different test compounds are differentially detected in a single system, e.g., through electrophoretic separation of the effects, or differential labeling which enables separate detection.

Assay components are commercially available, or derived from any of a variety of biological sources apparent to one of skill and as described, supra. Biological samples can also be derived from organisms or even human patients using well known techniques such as venipuncture or tissue biopsy. Where the biological material is derived from non-human animals, such as commercially relevant livestock, blood and tissue samples are conveniently obtained from livestock processing plants. Similarly, plant material used in the assays of the invention are conveniently derived from agricultural or horticultural sources. Alternatively, a biological sample can be from a cell or blood bank where tissue and/or blood are stored, or from an in vitro source such as a culture of cells. Techniques and methods for establishing a culture of cells for use as a source for biological materials are well known to those of skill in the art. Freshney *Culture of Animal Cells, a Manual of Basic Technique, Third Edition* Wiley-Liss, New York (1994) provides a general introduction to cell culture.

In addition to biological systems, the apparatus and methods of the invention are adaptable to chemical synthetic approaches. For example chemical synthetic methods for making proteins, nucleic acids, amino acids, polymers, organic compounds and the like are well known. In general, most chemical synthetic protocols employ fluid mixing to mix reactants, reagents and the like. As applied to the present invention, a source of reactants, reagents or the like is fluidly coupled to a microfluidic channel. The reactants or reagents, which optionally comprise labels, are mixed in a microchannel. After mixing, reaction rates, product concentrations, reactant concentrations, or the like are easily determined using the methods described herein. Representative mixtures can be aliquoted from one channel into a different channel for subsequent analysis, e.g., using the time-gated methods described supra. No attempt is made to describe all of the possible reactants, reactions or products which can be employed in the methods and devices of the invention; it is presumed that one of skill is generally familiar with such known methods, and that, upon review of this disclosure, could adapt these known assays to the present system.

In another embodiment, the concentration profiling of the present invention is used during the course of in-line reactions, e.g., amplification reactions such as PCR, LCR, and the like, to provide quantitative information regarding the amount of starting materials, such as PCR templates. Plugs of starting material, e.g., nucleic acid templates, are flowed through a channel, e.g., in a microfluidic device, e.g., during amplification. Amplification samples and reagents are added to the channel, e.g., from wells disposed within the device or from an external source, such as a capillary or micropipettor. For example, PCR reagents are typically added from reservoirs within the device and cDNA samples, e.g., prepared from various RNA samples are introduced into the device, e.g., from a sipper capillary, resulting in a nucleic acid sample plug. Alternatively, the RNA samples are introduced from an external source and converted to cDNA in the channels of the device. The cDNA sample plug diffuses at the edges, as described above, producing a concentration gradient outside the boundaries of the initial sample plug. Analysis of the concentration gradient, e.g., as described above, is optionally used to obtain quantitative information about how much RNA was present in the starting material. For example, differences in starting concentrations are optionally represented as variations in the width of the amplified product.

In-line PCR (polymerase chain reaction) is described, e.g., in U.S. Ser. No. 09/093,832, entitled "MICROFLUIDIC MATRIX LOCALIZATION APPARAUS AND METHODS" filed Jun. 8, 1998 by Tammy Burd Mehta. Thermocycling in microscale devices including thermocycling by joule heating, e.g., to perform PCR, is described in U.S. Pat. No. 5,965,410 entitled "ELECTRICAL CURRENT FOR CONTROLLING FLUID TEMPERATURES IN MICROCHANNELS" by Calvin Chow, Anne R. Kopf-Sill and J. Wallace Parce; in Ser. No. 08/977,528, filed Nov. 25, 1997; WO 98/45481 by Knapp et al., published Oct. 15, 1998, entitled, "CLOSED-LOOP BIOCHEMICAL ANALYZERS"; and, e.g., in Ser. No. 09/287,069, entitled INEFFICEIENT FAST PCR, filed Apr. 6, 1999 by Kopf-Sill; and by Kopp et al., Science 280:1046 (1998). In brief, energy is provided to heat fluids, e.g., samples, analytes, buffers and reagents, in desired locations of the substrates in an efficient manner by application of electric current to fluids in microchannels. Thus, the present invention optionally uses power sources that pass electrical current through a first channel region for heating purposes, as well as for material transport. In exemplary embodiments, fluid passes through a channel of a desired cross-section (e.g., diameter) to enhance thermal transfer of energy from the current to the fluid. The channels can be formed on almost any type of substrate material such as, for example, amorphous materials (e.g., glass, plastic, silicon), composites, multi-layered materials, combinations thereof, and the like. Alternatively, heating blocks or wandering channels are used to provide thermocycling instead of joule heating.

Detection of PCR products is carried out as described above or using any method of detection known to those of skill in the art. For example, TaqMan, molecular beacons, and Peptide nucleic acid (PNA) detection methods are optionally used to detect PCR products. Molecular beacons are described, e.g., in U.S. Pat. No. 6,037,130, by Tyagi, entitled "WAVELENGTH-SHIFTING PROBES AND PRIMERS AND THEIR USE IN ASSAYS AND KITS." Use of PNAs in microfluidic systems, is described, e.g., in U.S. Ser. No. 60/203,723, DETECTION OF PNA/DNA FORMATION BY FLUORESCENCE POLARIZATION, filed May 12, 2000 by Nikiforov et al.

Detected signals are typically computationally deconvoluted as described above to provide concentration profiles that reveal the amount of starting material or reactant present in the specimen, e.g., using library look-up tables constructed as described above. Utilizing the concentration profiles of the sample plugs in this way provides quantitative PCR in one step, e.g., with one set of cycles.

In other embodiments, quantitative measurements are made in a channel other than the one used for PCR, e.g., a parallel channel. For example, a sample plug is optionally directed into a first channel for amplification and into another channel, e.g., a parallel channel, for quantitative analysis rather than amplifying in-line. In another embodiment, dilution of the starting template is optionally used, instead of diffusion of the sipped sample plug, to analyze the concentration profile and width of the template plug.

As described above, the screening methods of the present invention are generally carried out in "microfluidic devices" or "microlaboratory systems," which allow for integration of the elements required for performing the assay, automation, and minimal environmental effects on the assay system, e.g., evaporation, contamination, human error, or the like. A number of devices for carrying out the assay methods of the invention are described in substantial detail herein. However, it will be recognized that the specific configuration of these devices will generally vary depending upon the type of assay and/or assay orientation desired. For example, in some embodiments, the screening methods of the invention can be carried out using a microfluidic device having two intersecting channels. For more complex assays or assay orientations, multichannel/intersection devices are optionally employed. The small scale, integratability and self-contained nature of these devices allows for virtually any assay orientation to be realized within the context of the microlaboratory system. In addition, it will be realized that the data correction methods herein are applicable to flowing systems generally, and not simply in microfluidic systems.

SOURCES OF ASSAY COMPONENTS AND INTEGRATION WITH MICROFLUIDIC FORMATS

Sources of modulators, reactants and substrates can be fluidly coupled to microchannels as noted herein in any of a variety of ways. In particular, those systems comprising sources of materials set forth in Knapp et al. "Closed Loop Biochemical Analyzers" (WO 98/45481; PCT/US98/06723) and Parce et al. "High Throughput Screening Assay Systems in Microscale Fluidic Devices" WO 98/00231 and, e.g., in 60/128,643 filed Apr. 4, 1999, entitled "Manipulation of Microparticles In Microfluidic Systems," by Mehta et al. are applicable.

In these systems, a "pipettor channel" (a channel in which components can be moved from a source to a microscale element such as a second channel or reservoir) is temporarily or permanently coupled to a source of material. The source can be internal or external to a microfluidic device comprising the pipettor channel. Example sources include microwell plates, membranes or other solid substrates comprising lyophilized components, wells or reservoirs in the body of the microscale unit or device and others.

For example, the source of a modulator or PCR reagent can be a microwell plate external to the body structure, having, e.g., at least one well with the selected cell type or reagent. Alternatively, reagent sources comprise one or more of: a well disposed on the surface of the body structure comprising the selected cell type, component, or reagent; a reservoir disposed within the body structure comprising the selected cell type, component or reagent; a container external to the body structure comprising at least one compartment comprising the selected particle type or reagent; or a solid phase structure comprising the selected cell type or reagent in lyophilized or otherwise dried form.

Figure 2:
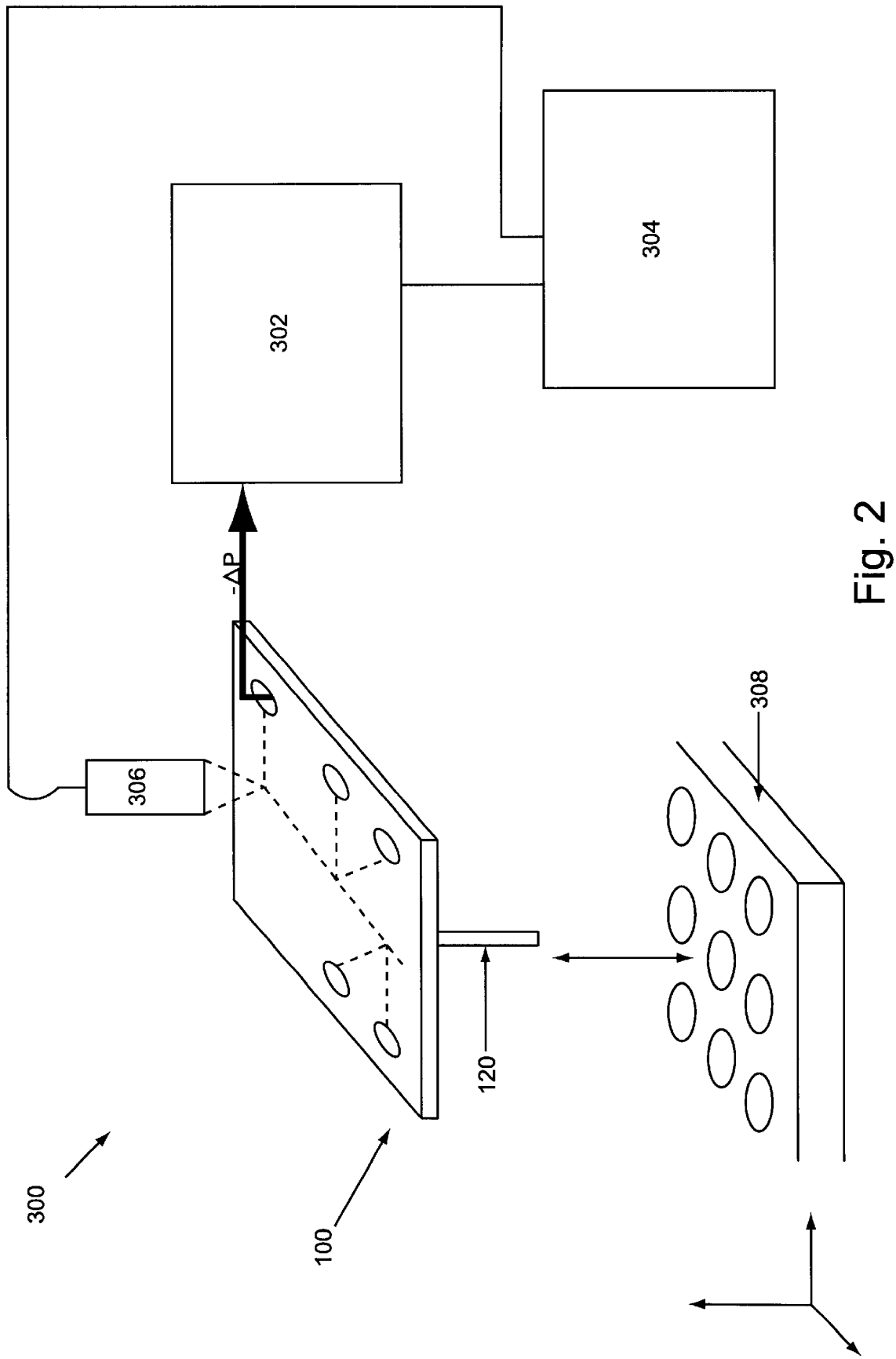
FIG. 2 is a schematic drawing of the integrated system of FIG. 1, further depicting incorporation of a microwell plate, a computer, a detector and a voltage/pressure controller.

A loading channel region is optionally fluidly coupled to a pipettor channel with a port external to the body structure, e.g., as depicted in FIGS. 1 and 2. The loading channel can be coupled to an electropipettor channel with a port external to the body structure, a pressure-based pipettor channel with a port external to the body structure, a pipettor channel with a port internal to the body structure, an internal channel within the body structure fluidly coupled to a well on the surface of the body structure, an internal channel within the body structure fluidly coupled to a well within the body structure, or the like. Additional example configurations are depicted in the figures herein.

The integrated microfluidic system of the invention can include a very wide variety of storage elements for storing reagents to be assessed. These include well plates, matrices, membranes and the like. The reactants or modulators are stored in liquids (e.g., in a well on a microtiter plate), or in lyophilized form (e.g., dried on a membrane or in a porous matrix), and can be transported to an array component of the microfluidic device using conventional robotics, or using an electropipettor or pressure pipettor channel fluidly coupled to a reaction or reagent channel of the microfluidic system.

In general, the test modulator compounds are separately introduced into the assay systems described herein, or at least introduced in relatively manageable pools of modulator materials (e.g., generally less than 100, and usually less than 10 potential modulators are mixed in a single source (e.g., a single well on a microtiter dish) coupled microfluidic system). The relative level of a particular modulator is then assessed in the presence of the relevant reactants and this relative level of function is then compared to a control system, which lacks an introduced modulator. Increases or decreases in relative reactant function (e.g., enzyme activity) are indicative that the test compound is an enhancer or an inhibitor of the particular function, respectively.

INTEGRATED SYSTEMS

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., reagent or modulator separation, extraction, purification, amplification, cellular activation, labeling reactions, dilutions, aliquotting, and the like. Similarly, downstream operations may include similar operations, including, e.g., separation of sample components, labeling of components, assays and detection operations, electrokinetic or pressure-based injection of components into contact with particle sets, or materials released from particle sets (e.g., as set forth in "MANIPULATION OF MICROPARTICLES IN MICROFLUIDIC SYSTEMS," by Mehta et al., 60/128,643, filed Apr. 4, 1999), or the like.

Assay Devices

Assay and detection operations include, without limitation, fluorogenic and non-fluorogenic enzyme assays, antibody-antigen binding assays, carbohydrate-protein binding assays, fluorescence assays, cell activity assays, probe interrogation assays, e.g., nucleic acid hybridization assays utilizing individual probes, free or tethered within the channels or chambers of the device and/or probe arrays having large numbers of different, discretely positioned probes, receptor/ligand assays, immunoassays, amplification assays, and the like. Any of these elements can be fixed free flowing or, in some aspects fixed to array members, or fixed, e.g., to channel walls, or the like.

As noted above, the assays of the present invention are carried out within fluidic channels, along which reactants are flowed. In some cases, the channels may simply be present in a capillary tube, e.g., a glass, fused silica, quartz or plastic capillary. The capillary channel is fluidly coupled to a source of reactants and/or reagents, which are then flowed along the capillary channel. In particularly preferred aspects, the channel is integrated into the body structure of a microfluidic device. As used herein, the term "microfluidic" generally refers to one or more fluid passages, channels, chambers or conduits which have at least one internal cross-sectional dimension, e.g., depth, width, length, diameter, etc., that is less than 500 µm, and typically between about 0.1 µm and about 500 µm.

In the devices of the present invention, the microscale channels or chambers preferably have at least one cross-sectional dimension between about 0.1 µm and 200 µm, more preferably between about 0.1 µm and 100 µm, and often between about 0.1 µm and 50 µm. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

The body structure of the microfluidic devices described herein typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion, or microscale cavity, substantially defines the channels and chambers of the device.

Suitable substrate materials for the body structure are generally selected based upon their compatibility with the conditions present in the particular operation to be performed by the device. Such conditions can include extremes of pH, temperature, salt concentration, and application of electrical fields. Additionally, substrate materials are also selected for their inertness to critical components of an analysis or synthesis to be carried out by the device. Examples of useful substrate materials include, e.g., glass, quartz and silicon as well as polymeric substrates, e.g. plastics, particularly polyacrylates. In the case of conductive or semi-conductive substrates, it is occasionally desirable to include an insulating layer on the substrate. This is particularly important where the device incorporates electrical elements, e.g., electrical fluid direction systems, sensors and the like. In the case of polymeric substrates, the substrate materials may be rigid, semi-rigid, or non-rigid, opaque, semi-opaque or transparent, depending upon the use for which they are intended. For example, devices which include an optical, spectrographic, photographic or visual detection element, will generally be fabricated, at least in part, from transparent materials to allow, or at least, facilitate that detection. Alternatively, transparent windows of, e.g., glass or quartz, are optionally incorporated into the device for these types of detection elements. Additionally, the polymeric materials optionally have linear or branched backbones, and may be crosslinked or non-crosslinked. Examples of polymeric materials include, e.g., polydimethylsiloxanes (PDMS), polyurethane, polyvinylchloride (PVC) polystyrene, polysulfone, polycarbonate and the like.

Instrumentation

In the present invention, the materials such as cells are optionally monitored and/or detected so that an activity can be determined. Depending on the label signal measurements, decisions are can be made regarding subsequent fluidic operations, e.g., whether to assay a particular modulator in detail to determine additional kinetic information.

The systems described herein generally include microfluidic devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Controllers

A variety of controlling instrumentation is optionally utilized in conjunction with the microfluidic devices described above, for controlling the transport and direction of fluids and/or materials within the devices of the present invention, e.g., by pressure-based and/or electrokinetic control.

For example, in many cases, fluid transport and direction are controlled in whole or in part, using pressure based flow systems that incorporate external or internal pressure sources to drive fluid flow. Internal sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357. As noted above, the systems described herein can also utilize electrokinetic material direction and transport systems. Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are described in U.S. Ser. No. 09/238,467 filed Jan. 28, 1999.

Typically, the controller systems are appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also used to provide for pressure-based or electrokinetic injection or withdrawal of material downstream of the region of interest to control an upstream flow rate. The same instrumentation and techniques described above are also utilized to inject a fluid into a downstream port to function as a flow control element.

Labels and Detectors

A "label" is any composition detectable by spectroscopic, photochemical, biochemical, immunochemical, electrical, optical or chemical means. Useful labels in the present invention include fluorescent dyes (e.g., fluorescein isothiocyanate, Texas red, rhodamine, and the like), luminescent dyes, colorimetric dyes, radiolabels (e.g., $^3$H, $^{125}$I, $^{35}$S, $^{14}$C, $^{32}$P, $^{33}$P, etc.), enzymes (e.g., horse-radish peroxidase, alkaline phosphatase etc.) colorimetric labels such as colloidal gold or colored glass or plastic (e.g. polystyrene, polypropylene, latex, etc.) beads. Label may be coupled directly or indirectly to the a component of the assay according to methods well known in the art. As indicated above, a wide variety of labels may be used, with the choice of label depending on sensitivity required, ease of conjugation with the compound, stability requirements, available instrumentation, and disposal provisions. Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, or cortisol, it can be used in conjunction with the labeled, naturally occurring anti-ligands. Alternatively, any haptenic or antigenic compound can be used in combination with an antibody (see, e.g., Coligan (1991) *Current Protocols in Immunology* Wiley/Greene, NY; and Harlow and Lane (1989) *Antibodies: A Laboratory Manual* Cold Spring Harbor Press, NY for a general discussion of how to make and use antibodies). The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol.

In some embodiments, a first and second label on the same or different components interact when in proximity (e.g., due to fluorescence resonance transfer), and the relative proximity of the first and second labels is determined by measuring a change in the intrinsic fluorescence of the first or second label. For example, the emission of a first label is sometimes quenched by proximity of the second label. Many appropriate interactive labels are known. For example, fluorescent labels, dyes, enzymatic labels, and antibody labels are all appropriate. Examples of interactive fluorescent label pairs include terbium chelate and TRITC (tetrarhodamine isothiocyanate), europium cryptate and Allophycocyanin, DABCYL and EDANS and many others known to one of skill. Similarly, two colorimetric labels can result in combinations which yield a third color, e.g., a blue emission in proximity to a yellow emission provides an observed green emission. With regard to preferred fluorescent pairs, there are a number of fluorophores which are known to quench one another. Fluorescence quenching is a bimolecular process that reduces the fluorescence quantum yield, typically without changing the fluorescence emission spectrum. Quenching can result from transient excited state interactions, (collisional quenching) or, e.g., from the formation of nonfluorescent ground state species. Self quenching is the quenching of one fluorophore by another; it tends to occur when high concentrations, labeling densities, or proximity of labels occurs. Fluorescent resonance energy transfer (FRET) is a distance dependent excited state interaction in which emission of one fluorophore is coupled to the excitation of another which is in proximity (close enough for an observable change in emissions to occur). Some excited fluorophores interact to form excimers, which are excited state dimers that exhibit altered emission spectra (e.g., phospholipid analogs with pyrene sn-2 acyl chains); see, Haugland (1996) *Handbook of Fluorescent Probes and Research Chemicals* Published by Molecular Probes, Inc., Eugene, OR. e.g., at chapter 13). Of course, as noted above, assays of interest can include velocitogenic rather than fluorogenic signal detection.

The devices herein optionally include signal detectors for detecting labels, e.g., which detect fluorescence, phosphorescence, radioactivity, pH, charge, absorbance, luminescence, temperature, magnetism or the like. Fluorescent detection is especially preferred.

The detector(s) optionally monitors one or a plurality of signals from downstream of an assay mixing point in which transmitter and a cell or other component with a transmitter receptor and the cell or other component with transporter activity are mixed. For example, the detector can monitor a plurality of optical signals which correspond in position to "real time" assay results.

Example detectors include photo multiplier tubes, a CCD array, a scanning detector, a galvo-scann or the like. Cells or other components which emit a detectable signal can be flowed past the detector, or, alternatively, the detector can move relative to the array to determine cell position (or, the detector can simultaneously monitor a number of spatial positions corresponding to channel regions, e.g., as in a CCD array).

The detector can include or be operably linked to a computer, e.g., which has software for converting detector signal information into assay result information (e.g., kinetic data of modulator activity), or the like.

Signals from arrays are optionally calibrated, e.g., by calibrating the microfluidic system by monitoring a signal from a known source.

A microfluidic system can also employ multiple different detection systems for monitoring the output of the system. Detection systems of the present invention are used to detect and monitor the materials in a particular channel region (or other reaction detection region). Once detected, the flow rate and velocity of cells in the channels is also optionally measured and controlled as described above. As described in PCT/US98/11969, correction of kinetic information based upon flow velocity can be used to provide accurate kinetic information.

Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device; a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to a computer (described in greater detail below), via an analog to digital or digital to analog converter, for transmitting detected light data to the computer for analysis, storage and data manipulation.

In the case of fluorescent materials such as substrates or products, the detector typically includes a light source which produces light at an appropriate wavelength for activating the fluorescent material, as well as optics for directing the light source through the detection window to the material contained in the channel or chamber. The light source can be any number of light sources that provides an appropriate wavelength, including lasers, laser diodes and LEDs. Other light sources required for other detection systems. For example, broad band light sources are typically used in light scattering/transmissivity detection schemes, and the like. Typically, light selection parameters are well known to those of skill in the art.

The detector can exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer.

Computer

As noted above, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

In the present invention, the computer typically includes software for the monitoring of materials in the channels. Additionally the software is optionally used to control electrokinetic or pressure modulated injection or withdrawal of material. The injection or withdrawal is used to modulate the flow rate as described above and for the selection of materials from an appropriate source of materials.

The computer also monitors reaction rates by calculating concentrations of reactants and products and kinetic information as set forth above, by storing libraries of signal profiles and comparing new signal profiles to the library of signal profiles as also set forth above. In general, one or more instruction sets are present in the computer, or on a computer-readable medium such as a computer hard-drive or CD-ROM which include instruction sets for calculating kinetic and concentration information using the above relationships. Libraries of signal profiles present in computer memory or on a computer-readable medium such as a computer hard-drive or CD-ROM are provided by the present invention and accessed by the system for calculation of kinetic and concentration information as described. The computer or the computer readable medium also optionally includes instruction sets for accurately calculating the concentrations of relevant reactants and products or for accurately calculating kinetic information based upon the relationships set forth above for velocities and concentrations of reactants and products into account in an electrokinetic system, e.g., where flux is conserved in a microfluidic system.

Typically, a computer commonly used to transform signals from the detection device into reaction rates will be a PC-compatible computer (e.g., having a central processing unit (CPU) compatible with ×86 CPUs, and running an operating system such as DOS™, OS/2 Warp™, WINDOWS/NT™, WINDOWS/NT™ workstation, or WINDOWS 98™), a Macintosh™ (running MacOS™), or a UNIX workstation (e.g., a SUN™ workstation running a version of the Solaris™ operating system, a LINUX operation system, or a PowerPC™ workstation), all of which are commercially common, and known to one of skill in the art. Data analysis software on the computer is then employed to determine the rate of formation of an analyte. Software for determining reaction rates is available, or can easily be constructed by one of skill using a standard programming language such as Visual Basic, Fortran, Basic, Java, or the like. The software is optionally designed to determine velocities, concentrations, flux relationships and the like, as described herein. Exemplar software processing steps for these operations are set forth in "APPARATUS & METHODS FOR CORRECTING FOR VARIABLE VELOCITY IN MICROFLUIDIC SYSTEMS," W098/56956 by Kopf-Sill et al. and similar processing steps can be used to assess the effects of modulators on reaction rates.

One of skill will immediately recognize that any, or all, of these components are optionally manufactured in separable modular units, and assembled to form an apparatus of the invention. See also, U.S. Ser. No. 08/691,632, supra. In particular, a wide variety of substrates having different channels, wells and the like are typically manufactured to fit interchangeably into the substrate holder, so that a single apparatus can accommodate, or include, many different substrates adapted to control a particular reaction. Similarly, computers, analyte detectors and substrate holders are optionally manufactured in a single unit, or in separate modules which are assembled to form an apparatus for manipulating and monitoring a substrate. In particular, a computer does not have to be physically associated with the rest of the apparatus to be "operably linked" to the apparatus. A computer is operably linked when data is delivered from other components of the apparatus to the computer. One of skill will recognize that operable linkage can easily be achieved using either electrically conductive cable coupled directly to the computer (e.g., a parallel, serial or modem cables), or using data recorders which store data to computer readable media (typically magnetic or optical storage media such as computer disks and diskettes, CDs, magnetic tapes, but also optionally including physical media such as punch cards, vinyl media or the like).

Example Integrated System

FIG. 1, panels A, B and C and FIG. 2 provide additional details regarding example integrated systems of the invention. As shown, body structure 102 has main channel 104 fabricated therein. A first reactant (e.g., an enzyme or substrate), or, more commonly, a modulator, is flowed from pipettor channel 120 towards reservoir 114, e.g., by applying a vacuum at reservoir 114, or by applying appropriate voltage gradients. Alternatively, a vacuum can be applied at reservoirs 106, 108, 112, 110, or through pipettor channel 120. A second reactant (e.g., a substrate or enzyme which corresponds to the first reactant), or a potential modulator or a different material such as a buffer or label can be flowed from wells 110 or 112 and into main channel 104, or from wells 106 or 108, depending on the exact format of the assay. Alternatively, materials can be flowed into these wells, e.g., when they are used as waste wells, or when they are coupled to a vacuum source or voltage gradient. Flow from wells 114, 112, 110, 106, or 108 can be performed by modulating fluid pressure, or by electrokinetic approaches as described (or both). The arrangement of channels depicted in FIG. 2 is only one possible arrangement out of many which are also appropriate and available for use in the present invention.

Reactants or modulators can be flowed from the enumerated wells, or can be flowed from a source external to body 102. As depicted, the integrated system can include pipettor channel 120, e.g., protruding from body 102, for accessing a source of reagents external to the microfludic system. Most typically, libraries of modulators are stored outside of the main microfluidic unit, e.g., in a microtiter dish or other convenient storage medium. For example, as further depicted in FIG. 3, pipettor channel 120 can access microwell plate 308 which includes potential modulators, controls, reactants or the like, e.g., in the wells of the plate. For example, a library of potential inhibitor/activator compounds/compositions can be stored in the wells of plate 308 for easy access by the system. Inhibitors or other reagents relevant to the assays can be flowed into channel 104 through pipettor channel 120. Detector 306 is in sensory communication with channel 104, detecting signals resulting, e.g., from the interaction of a transmitter with a transmitter receptor, as described above. Detector 306 is operably linked to computer 304, which digitizes, stores and manipulates signal information detected by detector 306, e.g., using any of the instruction sets described above, or any other instruction sets, e.g., for calculating kinetic or concentration relationships as described. Voltage/pressure controller 302 controls voltage, pressure, or both, e.g., at the wells of the system, or at vacuum couplings fluidly coupled to channel 104 (or the other channels noted above). Optionally, as depicted, computer 304 controls voltage/pressure controller 302. In one set of embodiments, computer 304 uses signal information to select further reaction parameters. For example, upon detecting inhibition by a potential modulator in a well from plate 308, the computer optionally directs withdrawal of additional aliquots of the potential modulator through pipettor channel 120, e.g., to deliver different concentrations of the potential modulator to the assay, e.g., to refine kinetic data (such as a dose-response curve) for the potential modulator.

In one aspect, the wells in the device of FIG. 1 (or a subset thereof) are connected to one or more pressure source(s) (i.e., one or more positive pressure sources and/or one or more negative pressure sources), as is the pipettor channel (e.g., at point 116). In this configuration, a first pressure (P1) level is found at the tip of pipettor channel 120, a second pressure level P2 is found in well 110, a third pressure level (P3) is found in well 112, a fourth pressure level (P4) is found in well 108, a fifth pressure level is found in well 106, a sixth pressure level is found at point 116, and a seventh pressure level is found at well 114. For convenience of illustration, well 110 comprises an enzyme, well 112 comprises a buffer, well 108 comprises a substrate, well 106 comprises a second buffer, and well 114 is connected to a primary vacuum source. Potential modulators are archived on microtiter plate 308 and accessed by the microfluidic unit through pipettor channel 120. In alternate embodiments, other reactants and other configurations of the above reagent/modulator configurations are substituted.

In this embodiment, the channels of the system also each have an associated resistance (R) and, during operation of the system, each channel has a flow rate of material (During pressure based flow, the bulk flow rate of the fluid at issue dictates the rate of flow of materials in the fluid. This is in contrast to electroosmotic flow, in which charge mass ratio and bulk fluid movement both influence the velocity of materials in a fluid).

Figure 4:
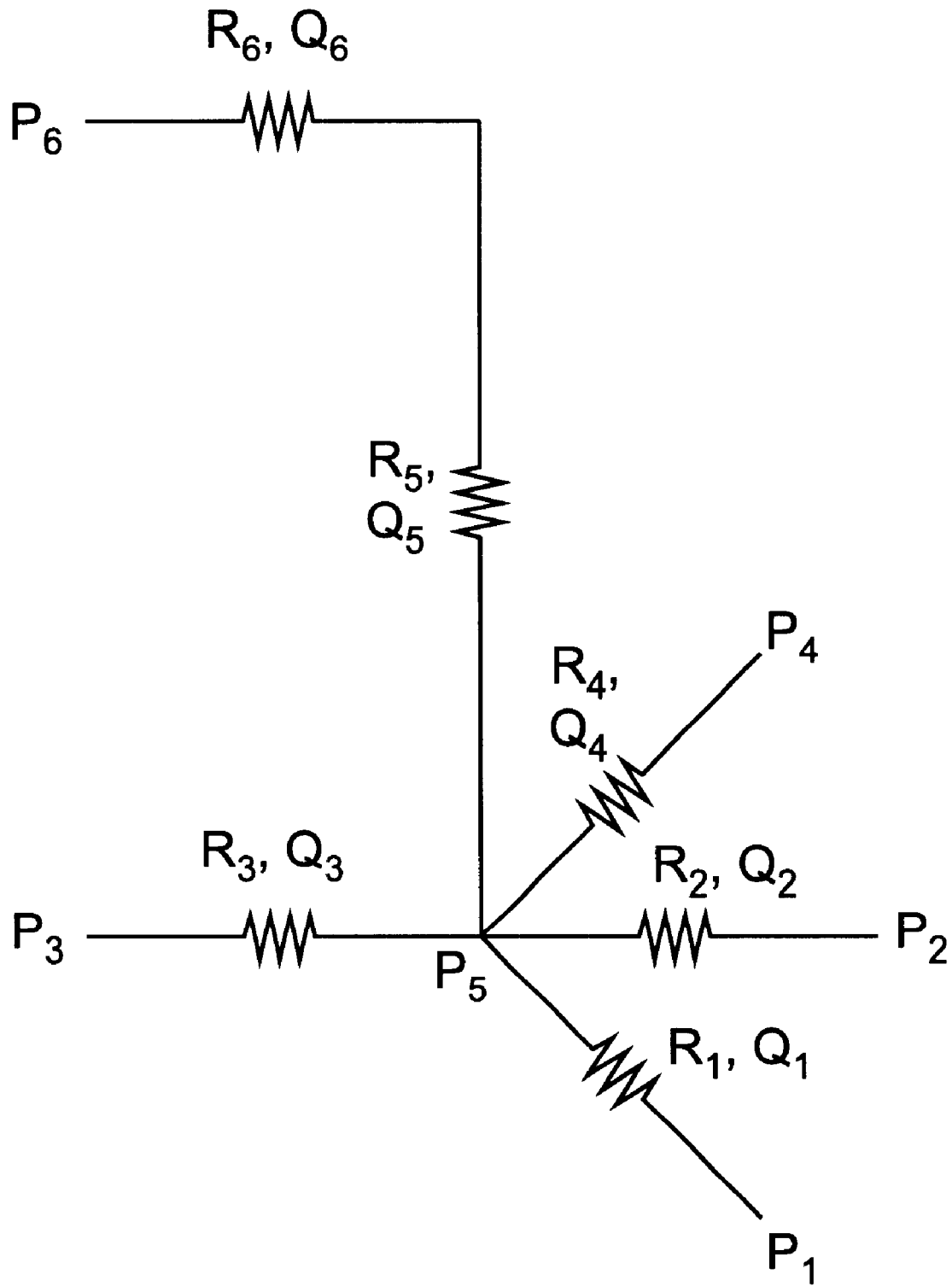
FIG. 4 is a schematic drawing of a pressure/flow/resistance diagram.

FIG. 4 schematically sets forth an alternate embodiment, with the layout in the form of a pressure/resistance/flow diagram (the system of FIG. 2 can be used to achieve the relevant pressure/resistance/flow relationships by applying pressure at a subset of the wells, or the diagram can represent a different microfluidic unit). The relationship between different pressure points ($P_1$–$P_6$ in this embodiment), channel resistances ($R_1$–$R_6$ in this embodiment) and flow rates ($Q_1$–$Q_5$ in this embodiment) can be determined, given information which is known or measured in the system.

For example, given $P_1$–$P_5$ (known, e.g., by measurement of pressure at the relevant points in the system, or by application of pressure at different wells or channels) and $R_1$–$R_5$ (measured and, e.g., fixed based upon channel geometry and the fluid in the system), Ohm's law and the Kinchoff rule are used to solve for flow rates e.g., by standard linear algebra.

For example, given $R_1, R_2, R_3, R_4, R_5, P_1, P_2, P_3, P_4, P_6$, it is possible to solve for $P_5, Q_1, Q_2, Q_4, Q_5$. By Ohm's law and the Kinchoff rule:

$P_{1-P5} = Q_1 R_1$ $P_2 - P_5 = Q_2 R_2$ $P_3 - P_5 = Q_3 R_3$ $P_4 - P_5 = Q_5 R_5$ $Q_5 = Q_1 + Q_2 + Q_3 + Q_4$ $P_5 = P_1 - Q_1 R_1$ $Q_2 = (P_2 - P_1 + Q_1 R_1)/R_2$ $Q_3 = (P_3 - P_1 + Q_1 R_1)/R_3$ $Q_4 = (P_4 - P_1 + Q_1 R_1)/R_4$ $Q_5 = Q_1 + (P_2 - P_1 + Q_1 R_1)/R_2 + (P_3 - P_1 + Q_1 R_1)/R_3 + (P_4 - P_1 + Q_1 R_1)/R_4$; thus $P_1 + P_2 + P_3 + P_4 - 4P_5 = Q_1 R_1 + Q_2 R_2 + Q_3 R_3 + Q_4 R_4 + Q_5 R_5$, and $$Q_1 = \frac{(P_1 - P_6) + (P_1 - P_2)\frac{R_5}{R_2} + (P_1 - P_3)\frac{R_5}{R_3} + (P_1 - P_4)\frac{R_5}{R_4}}{R_1\left(1 + \frac{R_5}{R_1} + \frac{R_5}{R_2} + \frac{R_5}{R_3} + \frac{R_5}{R_4}\right)}$$

This set of equations can be used to design channel geometry to have desired flow characteristics.

In general, it is desirable to control P1–P6 such that flow e.g., in channel 104 is constant, to permit incubation times for enzymes and substrates (or other reactants) to be constant, thereby simplifying kinetic calculations as performed herein. Similarly, the concentration of any given potential modulator is desirably modulated to provide kinetic information at multiple concentrations of modulator. The above pressure/resistance/flow relationships provide one way of controlling pressure and channel geometry to achieve constant flow rates in the microfluidic system.

Kits

Generally, the microfluidic devices described herein are optionally packaged to include reagents for performing the device's preferred function. For example, the kits can include any of microfluidic devices described along with assay components, reagents, sample materials, control materials, modulators or the like, optionally disposed within the microfluidic device. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (in one preferred embodiment, the device itself comprises a pipettor element, such as an electropipettor for introducing material into channels and chambers within the device). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like.

Kits also optionally include packaging materials or containers for holding microfluidic device, system or reagent elements.

The discussion above is generally applicable to the aspects and embodiments of the invention described in the claims.

Moreover, modifications can be made to the method and apparatus described herein without departing from the spirit and scope of the invention as claimed, and the invention can be put to a number of different uses including the following:

The use of a microfluidic system for performing the modulator assays set forth herein.

The use of a microfluidic system as described herein, wherein a biochemical system flows through one of said channels substantially continuously, providing for, e.g., sequential testing of a plurality of modulator compounds.

The use of electrokinetic and/or pressure-based fluid injection schemes in a microfluidic device as described herein to modulate or achieve flow of materials in channels of a microscale device, optionally in conjunction with pressure-based flow mechanisms.

The optional use of a combination of adsorbent materials, electrokinetic injection and pressure based flow elements in a microfluidic device as described herein to modulate or achieve flow of materials e.g., in the channels of the device.

An assay utilizing a use of any one of the microfluidic systems or substrates described herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were individually so denoted.

What is claimed is:

1. A method of determining the effect of a modulator on the interaction between at least two compounds at a plurality of modulator concentrations using a microfluidic device, the method comprising:

relying on the principles of Taylor dispersion and diffusion to estimate a concentration profile of the modulator in the flow direction of the modulator at a first detection point along a length of a first microchannel of the microfluidic device, the concentration profile including a plurality of modulator concentrations;

introducing the interacting compounds into the first microchannel at a location upstream from said first detection point, at least a portion of the interacting compounds interacting in the presence of the modulator as they travel through the first microchannel;

detecting the effect of the modulator on the interacting compounds at the first detection point thereby providing a modulation signal profile of the effect of the modulator on the interacting compounds; and correlating the estimated concentration profile of the modulator to the modulation signal profile to determine the effect of the modulator on the interaction between the two compounds at the plurality of modulator concentrations.

2. The method of claim 1, wherein determining the effect of the modulator on the interaction between the two compounds at the plurality of modulator concentrations is used to calculate a modulation constant of the modulator.

3. The method of claim 2, wherein the modulation constant is determined by comparison of the measured modulation signal profile to a library of a plurality of predetermined modulation signal profiles.

4. The method of claim 2, wherein the modulation constant is determined by estimating a modulation constant for the modulator, and comparing the measured modulation signal profile to a calculated modulation signal profile based on the estimated modulation constant and repeating the estimating a modulation constant step one or more times until the calculated modulation signal profile substantially resembles the estimated modulation signal profile.

5. The method of claim 2, wherein the modulation constant comprises an inhibition constant or an activation constant of the modulator.

6. The method of claim 1, wherein the estimating the concentration profile of the modulator comprises flowing a labeled dye into the first microchannel prior to the introducing step and measuring the concentration profile of the dye at the first detection point.

7. The method of claim 6, wherein the dye is chosen to have a molecular weight which is substantially equivalent to a molecular weight of the modulator.

8. The method of claim 1, wherein estimating the concentration profile of the modulator comprises determining a dispersion coefficient of the modulator.

9. The method of claim 8, wherein the estimating the concentration profile of the modulator comprises calculating the concentration profile using the relationship $C=\frac{1}{2}C_0\{erf[(h-x)/(2Dt)^{1/2}]+erf[(h-x)/(2Dt)^{1/2}]\}$, wherein $C_0$ is the initial concentration of the modulator at time 0 (t=0), erf is a selected error function and D is the coefficient of dispersion of the modulator.

10. The method of claim 9, wherein D is the sum of dispersion due to thermal diffusion and Taylor dispersion ($D_T$).

11. The method of claim 10, wherein Taylor dispersion ($D_T$) is a function of flow geometry of the first microchannel, flow velocity (u) and thermal diffusivity (D).

12. The method of claim 1, wherein the estimating the concentration profile of the modulator comprises flowing a modulator having a label associated therewith into the first microchannel prior to the introducing step and measuring the concentration profile of the labeled modulator at the detection point.

13. The method of claim 1, wherein said first and second interacting compounds comprise an enzyme and substrate.

14. The method of claim 1, wherein said first and second interacting compounds comprise a ligand-receptor binding pair.

15. The method of claim 1, wherein the modulator comprises an inhibitor.

16. The method of claim 1, wherein the modulator comprises an activity modulator.

17. The method of claim 1, further comprising introducing the first or second compounds into the first microchannel from a fluidly coupled pipettor channel.

18. The method of claim 17, wherein the pipettor channel is a pressure-controlled pipettor channel or an electropipettor.

19. The method of claim 1, wherein the modulation signal profile comprises an inhibition signal profile.

20. A method of determining the effect of a modulator on the interaction between at least two compounds at a plurality of modulator concentrations using a microfluidic device, the method comprising:

relying on the principles of Taylor dispersion and diffusion to estimate a plurality of concentration profiles of a modulator in the flow direction of the modulator at a first detection point along a length of a first microchannel of the microfluidic device, each concentration profile comprising a maximum concentration;

introducing a plurality of aliquots of modulator into the first microchannel at a location upstream from the first detection point, the aliquots having at least two different dwell times in the first microchannel;

introducing the interacting compounds into the first microchannel at a location upstream from said first detection point, at least a portion of the interacting compounds interacting in the presence of each aliquot of modulator as they travel through the first microchannel;

detecting the effect of each aliquot of the modulator on the interacting compounds at the first detection point thereby providing a plurality of modulation signal profiles of the effect of each modulator aliquot on the interacting compounds; and determining the modulation signal from each modulation signal profile of each modulator aliquot which corresponds to the maximum concentration of each concentration profile to determine the effect of the modulator on the interaction between the two compounds at the plurality of maximum modulator concentrations.

21. The method of claim 20, wherein introducing a plurality of aliquots of the modulator into the microchannel comprises varying the dwell time of a sample loader which loads the modulator into the first microchannel from a modulator source.

22. The method of claim 21, wherein the sample loader comprises one or more of an electrokinetic controller and a fluid pressure controller.

23. The method of claim 20, wherein introducing a plurality of aliquots of the modulator into the first microchannel comprises varying a flow rate of the plurality of aliquots of the modulator from a modulator source to vary the dwell times of the modulator in the first microchannel.

24. The method of claim 20, wherein determining the effect of the modulator on the interaction between the two compounds at the plurality of maximum modulator concentrations is used to calculate a modulation constant of the modulator.

25. The method of claim 20, wherein the estimating a plurality of concentration profiles of the modulator comprises flowing a labeled dye into the first microchannel at a plurality of dwell times and measuring the concentration profile of the dye at the first detection point for each of the plurality of dwell times.

26. The method of claim 25, wherein the dye is chosen to have a molecular weight which is substantially equivalent to a molecular weight of the modulator.

27. The method of claim 20, wherein said first and second interacting compounds comprise an enzyme and substrate.

28. The method of claim 20, wherein said first and second interacting compounds comprise a ligand-receptor binding pair.

29. The method of claim 20, wherein said modulator comprises an inhibitor.

30. The method of claim 20, wherein said modulator comprises an activity modulator.

* * * * *